(12) United States Patent
Otaka et al.

(10) Patent No.: US 10,337,849 B2
(45) Date of Patent: Jul. 2, 2019

(54) CAPACITIVE SENSOR

(71) Applicant: BANDO CHEMICAL INDUSTRIES, LTD., Kobe-shi, Hyogo (JP)

(72) Inventors: Hideo Otaka, Kobe (JP); Masaya Yonezawa, Kobe (JP); Yusuke Bessho, Kobe (JP)

(73) Assignee: BANDO CHEMICAL INDUSTRIES, LTD., Kobe-shi, Hyogo (JP)

( * ) Notice: Subject to any disclaimer, the term of this patent is extended or adjusted under 35 U.S.C. 154(b) by 19 days.

(21) Appl. No.: 15/519,956

(22) PCT Filed: Oct. 15, 2015

(86) PCT No.: PCT/JP2015/079124
§ 371 (c)(1),
(2) Date: Apr. 18, 2017

(87) PCT Pub. No.: WO2016/063783
PCT Pub. Date: Apr. 28, 2016

(65) Prior Publication Data
US 2017/0350686 A1 Dec. 7, 2017

(30) Foreign Application Priority Data

Oct. 22, 2014 (JP) ................................ 2014-215216

(51) Int. Cl.
*G01B 7/16* (2006.01)
*G01D 5/24* (2006.01)
(Continued)

(52) U.S. Cl.
CPC ............ *G01B 7/16* (2013.01); *G01D 5/2405* (2013.01); *G01L 1/14* (2013.01); *G01L 1/146* (2013.01);
(Continued)

(58) Field of Classification Search
CPC .. G01B 7/16; G01B 7/22; A61B 5/103; A61B 5/11; A61B 5/1107
See application file for complete search history.

(56) References Cited

U.S. PATENT DOCUMENTS 4,827,763 A    5/1989   Bourland et al.
5,693,886 A *  12/1997  Seimiya .................. G01L 1/142
                                                              73/718
(Continued)

FOREIGN PATENT DOCUMENTS

JP    2000-249773 A    9/2000
JP    2014-81355 A     5/2014
(Continued)

OTHER PUBLICATIONS

International Search Report dated Jan. 19, 2016 issued in corresponding PCT/JP2015/079124 application (2 pages).
(Continued)

*Primary Examiner* — David M. Gray
*Assistant Examiner* — Andrew V Do
(74) *Attorney, Agent, or Firm* — Millen, White, Zelano & Branigan, P.C.; William Nixon

(57) ABSTRACT

A capacitive sensor includes a sensor sheet having a central electrode layer and a measuring instrument. A first dielectric layer is laminated on the upper surface of the central electrode layer. A second dielectric layer is laminated on the lower surface of the central electrode layer. A first outer electrode layer is formed on the surface of the first dielectric layer. A second outer electrode layer is formed on the surface of the second dielectric layer. The central electrode layer and the first outer electrode layer face each other at a first detection portion. The central electrode layer and the second outer electrode layer face each other at a second detection portion. Capacitances of the detection portions change with deformation. The state of deformation of the sensor sheet is
(Continued)

measured on the basis of the total capacitance by adding the capacitances of the first detection portion and the second detection portion.

6 Claims, 10 Drawing Sheets

(51) Int. Cl.
  *G01L 1/14*   (2006.01)
  *G01N 27/22*  (2006.01)
  *G01R 27/26*  (2006.01)
  *G06F 3/041*  (2006.01)
  *G06F 3/044*  (2006.01)

(52) U.S. Cl.
  CPC ....... *G01N 27/227* (2013.01); *G01R 27/2617* (2013.01); *G06F 3/044* (2013.01); *G06F 3/0414* (2013.01)

(56) References Cited

U.S. PATENT DOCUMENTS

| | | | |
|---|---|---|---|
| 8,680,876 B2 * | 3/2014 | Kadono | G06F 3/041 |
| | | | 324/658 |
| 2006/0162464 A1 | 7/2006 | Hayashi et al. | |
| 2015/0268106 A1 | 9/2015 | Otaka et al. | |

FOREIGN PATENT DOCUMENTS

| | | |
|---|---|---|
| WO | 03/036247 A1 | 5/2003 |
| WO | 2014/050245 A1 | 4/2014 |

OTHER PUBLICATIONS

English Machine Translation of JP 2000-249773 A published Sep. 14, 2000.
Supplementary European Search Report dated Apr. 18, 2018 issued in corresponding EP 15852169.0 (7 pages).

\* cited by examiner

CROSS-SECTIONAL VIEW ALONG LINE B-B

CAPACITIVE SENSOR

TECHNICAL FIELD

The present invention relates to a capacitive sensor.

BACKGROUND ART

A capacitive sensor is a sensor which can detect concavo-convex shapes or the like of a measuring object from the capacitance change between a pair of electrode layers disposed so as to face each other, with a dielectric layer interposed therebetween.

Generally, capacitance in a capacitive sensor is represented by the following Formula (1):

$$C = \varepsilon_0 \varepsilon_r S/d \tag{1}$$

Here, C represents capacitance; $\varepsilon_0$ represents the permittivity of free space; $\varepsilon_r$ represents the relative permittivity of a dielectric layer; S represents the area of an electrode layer; and d represents the distance between electrodes.

Furthermore, Patent Literature 1 describes a capacitive sensor sheet including a dielectric layer formed from an elastomer; a top electrode layer and a bottom electrode layer that are formed on the top surface and the bottom surface of the dielectric layer, respectively. In this capacitive sensor sheet, since the dielectric layer is formed from an elastomer, the dielectric layer is capable of repeated elastic deformation. Furthermore, in regard to this capacitive sensor sheet, since the various electrode layers contain carbon nanotubes, the electrode layers can change their shapes in conformity with the deformation of the dielectric layer.

Therefore, the capacitive sensor sheet described in Patent Literature 1 can change its shape in conformity with the deformation or motion of a measuring object, even if the measuring object is flexible and has a high degree of elongation. Thus, the capacitance changes as a result of this deformation.

CITATION LIST

Patent Literature

Patent Literature 1: JP 2014-81355 A

SUMMARY OF INVENTION

Technical Problem

On the other hand, a conventional capacitive sensor includes, as described above, a condenser structure composed of a dielectric layer and electrode layers provided on both surfaces thereof, and the measured value of capacitance may vary depending on the use environment.

For example, in a case where an electrode layer is exposed, when this electrode layer is brought into contact with a conductor, the measured value of capacitance is largely fluctuated.

Thus, it is suggested in Patent Literature 1 that a protective layer is provided so that conduction between an electrode layer and an external member.

However, in a capacitive sensor which is presupposed to change its shape in conformity with deformation or motion of a measuring object, as suggested in Patent Literature 1, even if a protective layer is provided in order to secure flexibility (deformability) of the sensor sheet, the thickness of the protective layer has to be made thin.

In a case in which the thickness of the protective layer is small, there were occasions in which fluctuation of the measured value of capacitance caused by the use environment cannot be sufficiently suppressed.

According to the studies of the inventors of the present invention, it was confirmed that when electromagnetic wave noise such as electromagnetic noise or power supply noise caused by commercial power supplies penetrates into a measuring instrument, the measured value of capacitance fluctuates. For example, it has been found that when a capacitive sensor sheet is used, if a commercial power supply or the like is present nearby, capacitance may not be accurately measured.

Furthermore, in a case where a sensor sheet in which electrode layers (top electrode layer and bottom electrode layer) are respectively laminated on both surfaces of a dielectric layer as described in Patent Literature 1, it is obvious that in a case where a electrically connected conductor comes close to the various electrode layers (that is, in a case where conductors come close to the top electrode layer and the bottom electrode layer, and the electrode that has come close to the top electrode layer and the conductor that has come close to the bottom electrode layer are electrically connected), the measured value of capacitance thus measured becomes large.

The present invention was achieved in view of such circumstances, and it is an object of the invention to provide a capacitive sensor with which fluctuation in the measured value of capacitance caused by the use environment is small.

Solution to Problem

The capacitive sensor of the present invention comprises a sensor sheet and a measuring instrument, the sensor sheet including:

a central electrode layer;

a first dielectric layer laminated on the upper surface of the central electrode layer;

a second dielectric layer laminated on the lower surface of the central electrode layer;

a first outer electrode layer formed on the surface of the first dielectric layer on the opposite side of the central electrode layer; and a second outer electrode layer formed on the surface of the second dielectric layer on the opposite side of the central electrode layer, in which the first dielectric layer and the second dielectric layer are formed from elastomers, the part where the central electrode layer and the first outer electrode layer face each other is designated as a first detection portion, while the part where the central electrode layer and the second outer electrode layer face each other is designated as a second detection portion, the sensor sheet is reversibly deformable, and the capacitances of the first detection portion and the second detection portion change with deformation, and the measuring instrument being connected to the central electrode layer, the first outer electrode layer and the second outer electrode layer and measuring the capacitances of the first detection portion and the second detection portion, wherein the state of deformation of the sensor sheet is measured on the basis of the total capacitance by adding the capacitance of the first detection portion and the capacitance of the second detection portion.

The above-described capacitive sensor includes a sensor sheet that has a central electrode layer; and an outer electrode layer on either surface of the central electrode layer, with a dielectric layer interposed between the central electrode layer and the outer electrode layer. The total capacitance by adding the capacitance of the part where the central electrode layer and the first outer electrode layer face each other (capacitance of first detection portion), and the capacitance of the part where the central electrode layer and the second outer electrode layer face each other (capacitance of second detection portion) is measured, and the state of deformation of the sensor sheet is measured on the basis of the measured value. In the capacitive sensor, since the state of deformation of the sensor sheet is measured on the basis of the total capacitance of two detection portions, an excellent effect is provided, in which fluctuation in the measured value of capacitance caused by the use environment is not easily generated.

In regard to the capacitive sensor, it is preferable that the central electrode layer, the first outer electrode layer and the second outer electrode layer are all formed from an electroconductive composition containing carbon nanotubes.

According to the present configuration, the various electrode layers have excellent electric conductivity and are also suitable for changing shapes in conformity with deformation of the dielectric layers.

In regard to the capacitive sensor described above, it is preferable that the sensor sheet further includes at least one of a first protective layer laminated on the first outer electrode layer on the opposite side of the first dielectric layer side, and a second protective layer laminated on the second outer electrode layer on the opposite side of the second dielectric layer side.

According to the present configuration, the various electrode layers can be protected, and the measurement error for capacitance at the time of measurement can be more reliably reduced.

In regard to the capacitive sensor, it is preferable that the measuring instrument described above includes a circuit for measuring capacitance using the alternating current impedance. In this case, excellent repeat accuracy is obtained even in measurement using a high frequency signal, and when a high frequency signal is used, impedance does not become too large. Therefore, the measurement accuracy can be further increased, and the time required for measuring capacitance can be shortened.

Also, in a capacitive sensor having a measuring instrument that includes a circuit which measures capacitance using alternating current impedance as described above, it is preferable that the measuring instrument includes a CV conversion circuit, the central electrode layer is electrically connected to the CV conversion circuit side, and the first outer electrode layer and the second outer electrode layer are electrically connected to the alternating current signal generation side of the measuring instrument.

Furthermore, in a capacitive sensor having a measuring instrument that includes a circuit which measures capacitance using alternating current impedance as described above, it is also preferable that the measuring instrument includes a CF conversion circuit, the central electrode layer is electrically connected to the CF conversion circuit side, and the first outer electrode layer and the second outer electrode layer are grounded.

When capacitive sensors having these configurations are used, even if there is a noise source on any one side of the top surface side and the bottom surface side of the sensor sheet, fluctuation of the measured value of capacitance caused by the presence of the noise source can be prevented more reliably, and the capacitance of a detection portion can be more accurately measured.

Advantageous Effects of Invention

In the capacitive sensor of the present invention, fluctuation of the measured value of capacitance can be made very small.

DESCRIPTION OF EMBODIMENTS

Hereinafter, embodiments of the present invention will be described with reference to the drawings.

A capacitive sensor according to embodiments of the present invention comprises a sensor sheet and a measuring instrument, the sensor sheet including a central electrode layer; a first dielectric layer laminated on the upper surface of the central electrode layer; a second dielectric layer laminated on the lower surface of the central electrode layer; a first outer electrode layer formed on the surface of the first dielectric layer on the opposite side of the central electrode layer; and a second outer electrode layer formed on the surface of the second dielectric layer on the opposite side of the central electrode layer, in which the first dielectric layer and the second dielectric layer are formed from elastomers, the part where the central electrode layer and the first outer electrode layer face each other is designated as a first detection portion, the part where the central electrode layer and the second outer electrode layer face each other is designated as a second detection portion, the sensor sheet is reversely deformable, and the capacitances of the first detection portion and the second detection portion change with deformation, and the measuring instrument being connected to the central electrode layer, the first outer electrode layer and the second outer electrode layer and measuring the capacitances of the first detection portion and the second detection portion, wherein the state of deformation of the sensor sheet is measured on the basis of the total capacitance by adding the capacitance of the first detection portion and the capacitance of the second detection portion.

Figure 1:
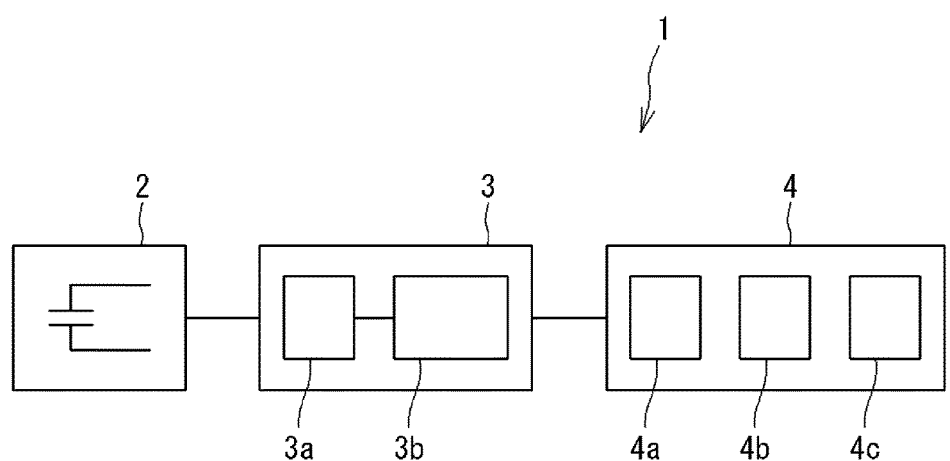
FIG. 1 is a schematic diagram illustrating an example of a capacitive sensor according to an embodiment of the present invention.

FIG. 1 is a schematic diagram illustrating an example of a capacitive sensor according to an embodiment of the present invention.

Figure 2A:
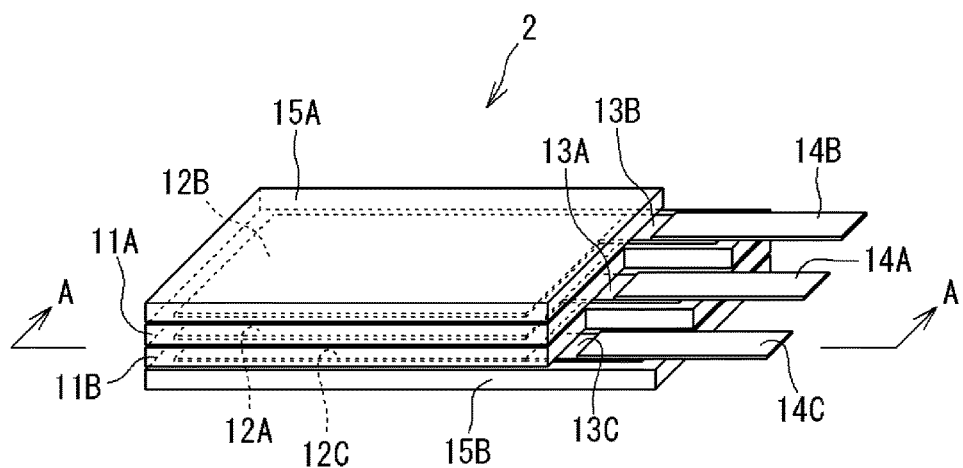
FIG. 2A is a perspective view schematically illustrating an example of a sensor sheet that constitutes a capacitive sensor according to an embodiment of the present invention.
Figure 2B:
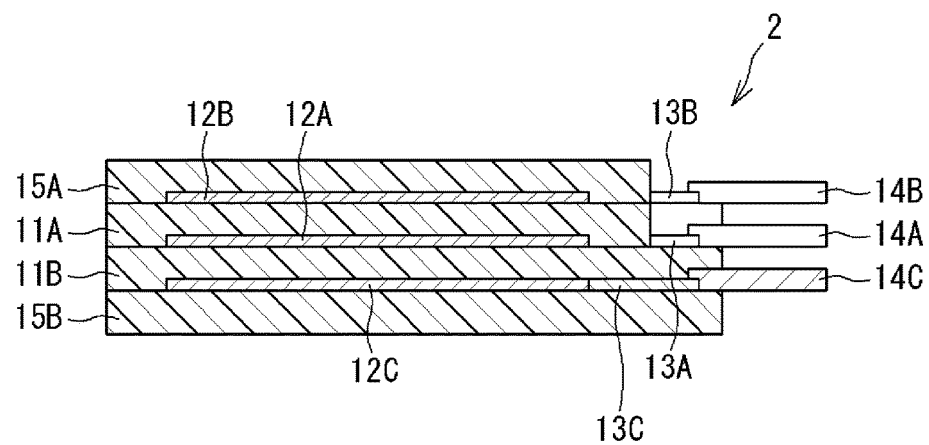
FIG. 2B is a cross-sectional view obtainable by cutting the sensor sheet along the line A-A shown in FIG. 2A.

FIG. 2A is a perspective view schematically illustrating an example of the sensor sheet that constitutes a capacitive sensor according to an embodiment of the present invention, and FIG. 2B is a cross-sectional view cut along the line A-A shown in FIG. 2A.

As illustrated in FIG. 1, a capacitive sensor 1 according to the present embodiment includes, as illustrated in FIG. 1, a sensor sheet 2 that detects capacitance; a measuring instrument 3 that is electrically connected to the sensor sheet 2 through an external conducting wire (lead wire or the like); and a display device 4 for displaying the measurement results obtained in the measuring instrument 3.

The measuring instrument 3 includes a Schmitt trigger oscillator circuit 3a for converting capacitance C to a frequency signal F; a F/V conversion circuit 3b that converts the frequency signal F to a voltage signal V; and a power supply circuit (not shown in the diagram).

The measuring instrument 3 converts the capacitance C detected in the detection portion of the sensor sheet 2 to a frequency signal F, subsequently further converts the frequency signal F to a voltage signal V, and transmits the voltage signal V to display device 4. As will be described below, the configuration of the measuring instrument 3 is not intended to be limited to such a configuration.

The display device 4 includes a monitor 4a; an arithmetic circuit 4b; and a memory unit 4c. The display device 4 displays the change in capacitance C measured at the measuring instrument 3, on the monitor 4a, and also stores the change in capacitance C as recorded data.

The sensor sheet 2 includes a sheet-like bottom dielectric layer (second dielectric layer) 11B formed from an elastomer; a central electrode layer 12A formed on the top surface (front surface) of the bottom dielectric layer 11B; a bottom electrode layer (second outer electrode layer) 12C formed on the bottom surface of the bottom dielectric layer 11B; a top dielectric layer (first dielectric layer) 11A laminated on the top side (upper side in FIGS. 2A and 2B) of the central electrode layer 12A; and a top electrode layer (first outer electrode layer) 12B formed on the top surface of the top dielectric layer 11A. Therefore, in the sensor sheet 2, the top dielectric layer 11A is laminated on the upper surface of the central electrode layer 12A, and the bottom dielectric layer 11B is laminated on the lower surface of the central electrode layer 12A.

Furthermore, the sensor sheet 2 includes a central conducting wire 13A joined to the central electrode layer 12A; a top conducting wire 13B joined to the top electrode layer 12B; a bottom conducting wire 13C joined to the bottom electrode layer 12C; a central connecting portion 14A mounted at the end of the central conducting wire 13A that is on the opposite side of the central electrode layer 12A; a top connecting portion 14B mounted at the end of the top conducting wire 13B that is on the opposite side of the top electrode layer 12B; and a bottom connecting portion 14C mounted at the end of the bottom conducting wire 13C that is on the opposite side of the bottom electrode layer 12C.

In the sensor sheet 2, a top protective layer (first protective layer) 15A is provided on the top side of the top dielectric layer 11A, and a bottom protective layer (second protective layer) 15B is provided on the bottom side of the bottom dielectric layer 11B.

The central electrode layer 12A, the top electrode layer 12B, and the bottom electrode layer 12C have the same planar view shape. The central electrode layer 12A and the top electrode layer 12B face each other in their entirety with the top dielectric layer 11A interposed therebetween, and the central electrode layer 12A and the bottom electrode layer 12C face each other in their entirety with the bottom dielectric layer 11B interposed therebetween. In the sensor sheet 2, the part where the central electrode layer 12A and the top electrode layer 12B face each other becomes a top detection portion (first detection portion), and the part where the central electrode layer 12A and the bottom electrode layer 12C face each other becomes a bottom detection portion (second detection portion).

In the sensor sheet described above, it is not necessarily required that the central electrode layer and the top electrode layer face each other in their entirety with a dielectric layer interposed therebetween, and the electrode layers may at least partially face each other. It is also not necessarily required that the central electrode layer and the bottom electrode layer face each other in their entirety with a dielectric layer interposed therebetween, and the electrode layers may at least partially face each other.

In the sensor sheet 2, the total capacitance by adding the capacitance of the first detection portion and the capacitance of the second detection portion is designated as the capacitance of the detection portion of the sensor sheet 2.

For this reason, in the sensor sheet 2, the top electrode layer 12B (top connecting portion 14B) and the bottom electrode layer 12C (bottom connecting portion 14C), in a state of being electrically connected to each other (short-circuited state), are connected to a terminal of the measuring instrument 3 though a lead wire or the like, and the central electrode layer 12A (central connecting portion 14A) is connected to another terminal of the measuring instrument 3 through a lead wire or the like.

Furthermore, in the sensor sheet 2, although not shown in the diagram, a pressure-sensitive adhesive layer may be formed in the outermost layer on the top side and/or the bottom side of the sensor sheet 2.

By having the pressure-sensitive adhesive layer formed, the sensor sheet can be used in a state of being attached to a measuring object.

In the sensor sheet 2, since the top dielectric layer 11A and the bottom dielectric layer 11B are together formed from elastomers, the dielectric layers can be deformed (stretched) in a surface direction. Furthermore, when the dielectric layers 11 (top dielectric layer 11A and bottom dielectric layer 11B) are deformed in a surface direction, the various electrode layers (central electrode layer 12A, top electrode layer 12B, and bottom electrode layer 12C), and the top protective layer 15A and the bottom protective layer 15B (hereinafter, the two may also be together referred to as protective layer) change their shapes in conformity with the deformation of the dielectric layers 11.

Along with deformation of the sensor sheet 2, the capacitances of the various detection portions change with a correlation between the capacitance and the amount of deformation of the dielectric layers (top dielectric layer 11A and bottom dielectric layer 11B). Accordingly, by detecting the change in capacitance, the amount of deformation of the sensor sheet 2 can be detected.

A capacitive sensor including the sensor sheet 2 can suppress fluctuation in the measured value of capacitance caused by noise, and even under a circumstance in which noise exists, or under a circumstance in which noise fluctuates at the time of measurement, the state of deformation of the sensor sheet can be accurately measured.

In a case in which a capacitive sensor is used, when the capacitive sensor is used in a place where electronic noise or power supply noise can easily penetrate as described above, or in an environment in which the electrode layers of the sensor sheet are brought into contact with or approach a conductor, the measured value of capacitance of the detection portion may fluctuate due to the circumstance of use.

For example, in a sensor sheet including a single dielectric layer and electrode layers respectively formed on the top surface and the bottom surface of the dielectric layer as disclosed in Patent Literature 1, the measured value of capacitance may be different depending on whether noise penetrates through the top side (whether the top side is close to the noise source), or noise penetrates through the bottom side (whether the bottom side is close to the noise source).

Furthermore, even in a case where conductors approach both the electrode layer on the top side and the electrode layer on the bottom side, and the conductor that has approached the conductor layer on the top side and the conductor that has approached the conductor layer on the bottom side are electrically connected (for example, in a case where both sides of a sensor sheet in which protective layers are laminated on electrode layers is brought into contact with water or the body, or in a case where both sides of a sensor sheet in which protective layers are laminated on electrode layers is interposed between electrically connected metal plates), the measured value of capacitance may be different. In this case, the capacitance between the electrode layer of the top side and the conductor approaching this, and the capacitance between the electrode layer on the bottom side and the conductor approaching this are added to the capacitance of the original detection portion of the sensor sheet, which is combined capacitance of two capacitances connected in series, and thereby measurement is made.

In contrast, in the capacitive sensor described above, the sensor sheet comprises the configuration described above, and the total capacitance by adding the capacitance of the first detection portion and the capacitance of the second detection portion is measured. That is, in the aforementioned sensor sheet, the structure of the detection portion (structure of the first detection portion and the second detection portion) is regarded as a structure in which two condensers are arranged in parallel, and measurement of the capacitance is implemented. Therefore, for example, in the capacitive sensor, both the top electrode layer (first outer electrode layer) and the bottom electrode layer (second outer electrode layer), in a state of being electrically connected (state of being short-circuited), are connected to a measuring instrument. In this case, in a case where noise penetrates through the top side (upper surface side) (top side approaches the noise source) as well as in a case where noise penetrates through the bottom side (lower surface side) (bottom side approaches the noise source), as long as the various electrode layers are connected to the measuring instrument in a predetermined direction, the measured values of capacitance become approximately the same values.

Furthermore, also in a case where conductors that are electrically connected to each other respectively approach the first outer electrode layer and the second outer electrode layer on both the top side and the bottom side of the sensor sheet (for example, being immersed in water, both sides of a sensor sheet having protective layers laminated thereon are brought into contact with the body, or a sensor sheet having protective layers laminated thereon is interposed between two sheets of connected metal plates), as long as the various electrode layers are connected to the measuring instrument in a predetermined direction, the measured values of capacitance become approximately the same values. In this case, it is because since the first outer electrode layer and the second outer electrode layer have the same potential, a route through which the capacitances between the respective outer electrode layers and the approached conductors is not formed, and the capacitances between the approaching conductors and the various outer electrode layers are not measured in an additive manner.

Therefore, as described above, in the capacitive sensor sheet according to the present embodiment, fluctuation in the measured value of capacitance caused by noise can be suppressed.

According to the present invention, when it is said that a conductor approaches an outer electrode layer, this is a concept that includes a case in which an electroconductive member such as a metal member approaches, a case in which a biological surface approaches, a case in which a liquid having electric conductivity, such as water, sweat or body fluid, attaches to the outer electrode layer, and the like.

Hereinafter, various members that are included in the capacitive sensor will be described in detail.

In the following description, in a case where it is not particularly necessary to distinguish between a first dielectric layer and a second dielectric layer in connection with the explanation on those layers, the layers may be simply described as "dielectric layer". In a case in which it is not particularly necessary to distinguish various electrode layers in connection with the explanation on a central electrode layer, a first outer electrode layer (top electrode layer) and a second outer electrode layer (bottom electrode layer), the layers may be simply described as "electrode layer".

<Sensor Sheet>

<<Dielectric Layer (First Dielectric Layer and Second Dielectric Layer)>>

The sensor sheet described above includes a first dielectric layer and a second dielectric layer, both of which are formed from elastomers. The first dielectric layer and the second dielectric layer can be formed using elastomer compositions. The first dielectric layer and the second dielectric layer may be formed using the same elastomer composition, or may be formed using different elastomer compositions. It is preferable that the first dielectric layer and the second dielectric layer are formed using the same elastomer composition. It is because when the dielectric layers deform, they exhibit similar behavior.

The dielectric layers are sheet-like products formed using elastomer compositions, and can reversibly deform such that the area of the top and bottom surfaces change. The top and bottom surfaces of a dielectric layer mean the top surface (front surface) and the bottom surface of the dielectric layer.

The elastomer composition may be a composition including an elastomer and other optional components as necessary.

Examples of the elastomer include natural rubber, isoprene rubber, nitrile rubber (NBR), ethylene-propylene rubber (EPDM), styrene-butadiene rubber (SBR), butadiene rubber (BR), chloroprene rubber (CR), silicone rubber, fluorine rubber, acrylic rubber, hydrogenated nitrile rubber, and urethane elastomer. These may be used singly, or two or more kinds thereof may be used in combination.

Among these, urethane elastomer and silicone rubber are preferred. It is because these rubbers have small permanent set (or permanent elongation). Furthermore, in a case where the electrode layers contain carbon nanotubes, urethane elastomer is particularly preferred because urethane elastomer has excellent adhesion to carbon nanotubes compared to silicone rubber.

The urethane elastomer is a product obtainable as a result of a reaction between at least a polyol component and an isocyanate compound. Specific examples of the urethane elastomer include, for example, an olefin-based urethane elastomer containing an olefin-based polyol as a polyol component; an ester-based urethane elastomer containing an ester-based polyol as a polyol component; an ether-based urethane elastomer containing an ether-based polyol as a polyol component; a carbonate-based urethane elastomer containing a carbonate-based polyol as a polyol component; and a castor oil-based urethane elastomer containing a castor oil-based polyol as a polyol component. These may be used singly, or two or more kinds thereof may be used in combination. The urethane elastomer may be a product obtained by using two or more kinds of the above-mentioned polyol components in combination.

Examples of the olefin-based polyol include EPOL (manufactured by Idemitsu Kosan Co., Ltd.).

Examples of the ester-based polyol include POLYLITE 8651 (manufactured by DIC Corp.).

Examples of the ether-based polyol include polyoxytetramethylene glycol, PTG-2000SN (manufactured by Hodogaya Chemical Co., Ltd.), polypropylene glycol, PREMINOL S3003 (manufactured by Asahi Glass Co., Ltd.), and PANDEX GCB-41 (manufactured by DIC Corp.).

The isocyanate component is not particularly limited, and any conventionally known isocyanate component can be used.

When the urethane elastomer is synthesized, a chain extending agent, a crosslinking agent, a catalyst, a vulcanizing agent, and the like may be added to the reaction system.

The elastomer composition may include, in addition to the elastomer, additives such s a plasticizer, an antioxidant, an age resistor, and a colorant; a dielectric filler, and the like.

The average thickness of the dielectric layers (respective average thicknesses of the top dielectric layer and the bottom dielectric layer) are preferably 10 to 1,000 μm, and more preferably 30 to 200 μm, from the viewpoint of increasing capacitance C and thus promoting an increase in detection sensitivity, and from the viewpoint of promoting an enhancement of followability for a measuring object.

The respective thicknesses of the top dielectric layer and the bottom dielectric layer may be the same or may be different; however, it is preferable that the thicknesses are the same.

It is preferable that the dielectric layers are deformable such that the areas (area of the top surface of the top dielectric layer and the area of the bottom surface of the bottom dielectric layer) at the time of deformation increases by 30% or more from an unelongated state. It is because when the dielectric layers have such characteristics, in a case where the above-described sensor sheet is used in a state of being attached to a measuring object, the dielectric layers are suitable for changing their shapes in conformity with the deformation of the measuring object or the like.

Here, when it is said that a dielectric layer is deformable such that the area increases by 30% or more, it is implied that the dielectric layer does not break even if a load is applied and the area is increased by 30%, and when the load is removed, the dielectric layer is restored to an original state (that is, being within an elastic deformation range). Regarding the range of possible deformation of area of the dielectric layer, it is more preferable that the dielectric layer is deformable such that the area increases by 50% or more; it is even more preferable that the dielectric layer is deformable such that the area increases by 100% or more; and it is particularly preferable that the dielectric layer is deformable such that the area increases by 200% or more.

The range of possible deformation in the surface direction of the dielectric layer can be controlled by design (material, shape or the like) of the dielectric layer.

The relative permittivity at normal temperature of the dielectric layer is preferably 2 or higher, and more preferably 5 or higher. If the relative permittivity of the dielectric layer is less than 2, capacitance of the detection portions becomes smaller, and sufficient sensitivity as a sensor sheet may not be obtained.

Young's modulus of the dielectric layer is preferably 0.1 to 10 MPa. If this Young's modulus is less than 0.1 MPa, the dielectric layer becomes too soft, high quality processing is difficult, and sufficient measurement accuracy may not be obtained. On the other hand, if Young's modulus is more than 10 MPa, the dielectric layer becomes too hard, and when the measuring object is about to change its shape, there is a risk that deformation thereof may be inhibited.

Hardness of the dielectric layer is preferably 0° to 30° as the hardness determined using a Type A durometer according to JIS K 6253 (JIS A hardness), or preferably 10° to 55° as the hardness determined using a Type C durometer according to JIS K 7321 (JIS C hardness).

If the dielectric layer is too soft, high quality processing is difficult, and sufficient measurement accuracy may not be secured. On the other hand, if the dielectric layer is too hard, there is a risk that deformation of the measuring object may be inhibited.

<<Electrode Layers (Central Electrode Layer, First Outer Electrode Layer (Top Electrode Layer), and Second Outer Electrode Layer (Bottom Electrode Layer))>>

The electrode layers described above (central electrode layer, first outer electrode layer, and second outer electrode layer) are all formed from electroconductive compositions containing electrically conductive materials.

Here, the respective electrode layers may be formed from electroconductive compositions having the same composition, or may be formed from electroconductive compositions having different compositions.

Examples of the electrically conductive material include carbon nanotubes, graphene, carbon nanohorns, carbon fibers, electroconductive carbon black, graphite, metal nanowires, metal nanoparticles, and electroconductive polymers. These may be used singly, or two or more kinds thereof may be used in combination.

The electrically conductive material is preferably carbon nanotubes. It is because carbon nanotubes are adequate for the formation of an electrode layer that changes its shape in conformity with the deformation of a dielectric layer.

Regarding the carbon nanotubes, known carbon nanotubes can be used. The carbon nanotubes may be single-walled carbon nanotubes (SWNT), or may be double-walled carbon nanotubes (DWNT) or multi-walled carbon nanotubes (MWNT) having three or more layers (in the present specification, both are collectively referred to simply as multi-walled carbon nanotubes). Regarding the carbon nanotubes, two or more kinds of carbon nanotubes having different number of layers may be used in combination.

The shape (average length, fiber length, and aspect ratio) of the carbon nanotubes is not particularly limited, and the shape may be appropriately selected after comprehensively considering the purpose of use of the capacitive sensor, electric conductivity or durability required from the sensor sheet, and the treatment or cost for forming an electrode layer.

The average length of the carbon nanotubes is preferably 10 µm or more, and more preferably 50 µm or more. It is because an electrode layer formed using such carbon nanotubes having a long fiber length has excellent electric conductivity, and the electrode layer exhibits excellent characteristics such as that when the electrode layer changes its shape in conformity with the deformation of a dielectric layer (particularly when elongated), electrical resistance is hardly increased, and even if the electrode layer is subjected to repeated stretch, the electrode layer exhibits small variations in electrical resistance.

In contrast, if the average length of the carbon nanotubes is less than 10 µm, electrical resistance may increase along with a deformation of the electrode layer, or the variation in the electrical resistance may increase when the electrode layer is subjected to repeated stretch. Particularly, in a case where the amount of deformation of the sensor sheet (dielectric layer) becomes large, such inappropriateness may easily occur.

A preferred upper limit of the average length of the carbon nanotubes is 1,000 µm. Currently, production and purchase of carbon nanotubes having an average length of more than 1,000 µm is practically infeasible. Furthermore, as will be described below, it is because in a case where an electrode layer is formed by applying a dispersion liquid of carbon nanotubes, since carbon nanotubes has unsatisfactory dispersibility, conductive paths are not easily formed, and consequently, there is a risk that the electrode layer may acquire insufficient electric conductivity.

The lower limit of the average length of the carbon nanotubes is more preferably 100 µm, and the upper limit is more preferably 600 µm. When the average length of the carbon nanotubes is within the above-described range, excellent characteristics such as that excellent electric conductivity is obtained, electrical resistance of the electrode layer is hardly increased at the time of elongation, and the variation in electrical resistance at the time of repeated stretch is small, can be more reliably secured to a higher level.

The fiber length of the carbon nanotubes may be determined by observing the carbon nanotubes with an electron microscope, and measuring the fiber length from the observation image.

The average length of the carbon nanotubes may be determined by, for example, calculating the average value based on the fiber lengths of the carbon nanotubes at 10 sites randomly selected from observation images of the carbon nanotubes.

The average fiber length of the carbon nanotubes is not particularly limited; however, the average fiber length is preferably 0.5 to 30 nm.

If the fiber length is less than 0.5 nm, dispersion of the carbon nanotubes becomes poor, and as a result, conductive paths do not spread, and electric conductivity of the electrode layer may become insufficient. On the other hand, if the fiber length is more than 30 nm, the number of carbon nanotubes becomes smaller even at the same weight, and electric conductivity may become insufficient. The average fiber length of the carbon nanotubes is more preferably 5 to 20 nm.

Regarding the carbon nanotubes, multi-walled carbon nanotubes are preferred to single-walled carbon nanotubes.

If single-walled carbon nanotubes are used, even in a case where carbon nanotubes having an average length in the above-mentioned preferred range are used, electrical resistance may become high, electrical resistance may significantly increase at the time of elongation, or electrical resistance may be significantly vary at the time of repeated stretch.

The reason for this is speculated to be as follows. Since single-walled carbon nanotubes are usually synthesized as a mixture of metallic carbon nanotubes and semiconductive carbon nanotubes, it is speculated that the presence of these semiconductive carbon nanotubes is causative of increased electrical resistance, significant increase of electrical resistance at the time of elongation, or significant variation of electrical resistance at the time of repeated stretch.

When metallic carbon nanotubes are semiconductive carbon nanotubes are separated, and metallic single-walled carbon nanotubes having a long average length are used, there is a possibility that an electrode layer having similar electrical characteristics as in the case of using multi-walled carbon nanotubes having a long average length may be formed. However, separation of metallic carbon nanotubes and semiconductive carbon nanotubes is not easy (particularly, for carbon nanotubes having a long fiber length), and a complicated operation is needed for the separation of the two. Therefore, even from the viewpoint of the ease of operation at the time of forming an electrode layer and from the viewpoint of economic efficiency, multi-walled carbon nanotubes are preferred as the carbon nanotubes, as described above.

It is preferable that the carbon nanotubes have a carbon purity of 99% by weight or more. Carbon nanotubes may include catalytic metals, dispersants and the like during the production process therefor, and thus, in a case where carbon nanotubes containing components other than these carbon nanotubes (impurities) in large quantities are used, a decrease in electric conductivity or variation of electrical resistance may occur.

The method for producing the carbon nanotubes is not particularly limited, and the carbon nanotubes may be produced by a conventionally known production method. However, it is preferable that carbon nanotubes produced by a substrate growth method are preferred.

A substrate growth method is a kind of CVD methods, and is a method for producing carbon nanotubes by supplying a carbon source to a metal catalyst applied on a substrate, and thereby growing carbon nanotubes. Since the substrate growth method is a production method suitable for producing carbon nanotubes having a relatively long fiber length and having an even fiber length, this method is suitable for the carbon nanotubes that are used in the electrode layer.

In a case in which the carbon nanotubes are produced by a substrate production method, the fiber length of the carbon nanotubes is substantially the same as the length of growth of the CNT forest. Therefore, in a case where the fiber length of carbon nanotubes is measured using an electron microscope, it is desirable to measure the length of growth of the CNT forest.

The electroconductive composition may also include, for example, a binder component in addition to the electroconductive material such as carbon nanotubes.

The binder component functions as a binding material. Therefore, when the binder component is incorporated, the adhesion between the electrode layer and the dielectric layer, and the strength of the electrode layer itself can be enhanced.

Furthermore, when an electrode layer is formed by a method as described below, scattering of the electroconductive material such as carbon nanotubes can be suppressed, and therefore, safety at the time of forming an electrode layer can also be increased.

Examples of the binder component include butyl rubber, ethylene-propylene rubber, polyethylene, chlorosulfonated polyethylene, natural rubber, isoprene rubber, butadiene rubber, styrene-butadiene rubber, polystyrene, chloroprene rubber, nitrile rubber, polymethyl methacrylate, polyvinyl acetate, polyvinyl chloride, acrylic rubber, and a styrene-ethylene-butylene-styrene block copolymer (SEBS).

Furthermore, regarding the binder component, raw rubber (natural rubber or synthetic rubber in a state of being unvulcanized) can also be used. When a material having relatively weak elasticity, such as raw rubber, is used, followability of an electrode layer to the deformation of a dielectric layer can also be increased.

It is particularly preferable that the binder component is of the same kind as the elastomer that constitutes the dielectric layer. It is because the adhesion between the dielectric layer and the electrode layer can be noticeably enhanced.

The electroconductive composition may further include various additives in addition to the electroconductive material such as carbon nanotubes and the binder component.

Examples of the additives include a dispersant for increasing dispersibility of the electroconductive material, a cross-linking agent for the binder component, a vulcanization accelerating agent, a vulcanization aid, an age resistor, a plasticizer, a softening agent, and a colorant.

In the sensor sheet described above, in a case where the electroconductive material is carbon nanotubes, the electrode layer may be substantially formed from carbon nanotubes only. In this case, too, sufficient adhesion between the electrode layer and the dielectric layer can be secured. Carbon nanotubes and the dielectric layer strongly adhere to each other by van der Waals force or the like.

The content of the carbon nanotubes in the electrode layer is not particularly limited as long as the carbon nanotubes are included at a concentration at which electric conductivity is manifested. In a case in which a binder component is incorporated, the content of the carbon nanotubes may vary depending on the kind of the binder component; however, the content is preferably 0.1% to 100% by weight with respect to the total solid content of the electrode layer.

When the content of the carbon nanotubes is increased, electric conductivity of the electrode layer can be enhanced. Therefore, even if the electrode layer is made thin, required electric conductivity can be secured, and as a result, it becomes easier to make the electrode layer thinner or to secure flexibility of the electrode layer.

The average thickness of the electrode layer (respective average thicknesses of the various electrode layers) is preferably 0.1 to 10 μm. When the average thickness of the electrode layer is in the range described above, superior followability of the electrode layer to deformation of the dielectric layer can be manifested.

On the other hand, if the average thickness is less than 0.1 μm, there is a risk that electric conductivity may be insufficient, and the measurement accuracy as a sensor sheet may be decreased. On the other hand, if the average thickness is more than 10 μm, the sensor sheet becomes hard due to the reinforcement effect of the electroconductive material such as carbon nanotubes, stretchability of the sensor sheet is decreased, and shape change in conformity with deformation or movement of the measuring object may be inhibited.

Furthermore, if the sensor sheet becomes hard, deformation or the like of the measuring object itself may be inhibited.

The average thickness of the electrode layer can be measured using, for example, a laser microscope (for example, manufactured by Keyence Corp., VK-9510). Specifically, an electrode layer formed on the surface of a dielectric layer is scanned in the thickness direction in steps of 0.01 μm, a three-dimensional shape of the surface of the dielectric layer is measured, subsequently the average height of a rectangular region having a size of 200 μm in length× 200 μm in width is measured from a region where the electrode layer is laminated on the dielectric layer and a region where the electrode layer is not laminated on the dielectric layer, and the level difference of the average heights may be designated as the average thickness of the electrode layer.

There are no particular limitations on the respective electric conductivity of the central electrode layer, the top electrode layer and the bottom electrode layer that constitute the sensor sheet.

<<Protective Layer>>

It is preferable that the sensor sheet has protective layers (top protective layer and bottom protective layer) laminated thereon, as shown in the example illustrated in FIGS. 2A and 2B. By having the protective layers provided thereon, the top electrode layer, the bottom electrode layer and the like can be electrically insulated from the outside. Also, by having the protective layers provided thereon, strength and durability of the sensor sheet can be increased.

The material of the protective layer is not particularly limited, and the material may be appropriately selected according to the required characteristics. Specific examples of the material for the protective layer include, for example, an elastomer composition similar to the material for the dielectric layer.

<<Others>>

The sensor sheet usually has a central conducting wire, a top conducting wire and a bottom conducting wire, all of which are connected to the various electrode layers, as shown in the example illustrated in FIGS. 2A and 2B.

These various conducting wires may be any conducting wires that do not inhibit shape change of the dielectric layer, and that maintain electric conductivity even if the dielectric layer is deformed. Specific examples of the various conducting wires include, for example, a conductor formed from an electroconductive composition similar to the electrode layer described above.

Furthermore, it is preferable that the various conducting wires have narrow widths to the extent that necessary electric conductivity is secured.

At the end of each of the various conducting wires on the opposite side of the electrode layers, a connecting portion for connecting to an external conducting wire (a central connecting portion, a top connecting portion, or a bottom connecting portion) is usually formed, as shown in the example illustrated in FIGS. 2A and 2B. Examples of these various connecting portions include connecting portions formed using copper foil or the like.

As described above, the sensor sheet may have a pressure-sensitive adhesive layer formed at the outermost layer on the bottom side of the sensor sheet. Thereby, the sensor sheet can be attached to a measuring object through this pressure-sensitive adhesive layer.

The pressure-sensitive adhesive layer is not particularly limited, and examples thereof include layers formed from an acrylic pressure-sensitive adhesive, a rubber-based pressure-sensitive adhesive, a silicone-based pressure-sensitive adhesive, and the like.

Here, the various pressure-sensitive adhesives may be solvent type adhesives, emulsion type adhesives, or hot melt type adhesives. The pressure-sensitive adhesive may be appropriately selected and used according to the use embodiment of the capacitive sensor and the like. However, the pressure-sensitive adhesive layer needs to have flexibility that does not inhibit stretch of the dielectric layer.

The pressure-sensitive adhesive layer may also be formed at the top outermost layer of the sensor sheet.

When the sensor sheet is subjected to repetition of 1,000 cycles of stretch, for which a cycle of elongating the sensor sheet 100% in a uniaxial direction from an unelongated state and then returning the sensor sheet to an unelongated state is defined as one cycle, it is preferable that the change ratio of electrical resistance of the electrode layer at the time of 100% elongation of the $1,000^{th}$ cycle with respect to the electrical resistance of the electrode layer at the time of 100% elongation of the second cycle, (absolute value of [electrical resistance value at the time of 100% elongation of the $1,000^{th}$ cycle]-[electrical resistance value at the time of 100% elongation of the second cycle]/[electrical resistance value at the time of 100% elongation of the second cycle]× 100), is small. Specifically, the change ratio is preferably 10% or less, and more preferably 5% or less.

Here, the reason why the electrical resistance of the electrode layer after the second cycle, not the first cycle, is applied as the object of evaluation, is that at the time of the first elongation (first cycle) of elongating the sensor sheet from an unelongated state, the behavior of the electrode layer (mode of fluctuation in electrical resistance) at the time of elongation is greatly different from the behavior at the time of stretch after the second elongation (second cycle). Regarding a cause for this, it is speculated that after a sensor sheet is produced, the state of the electroconductive material such as carbon nanotubes that constitute the electrode layer is stabilized for the first time by elongating the sensor sheet one time.

Next, the method for producing the aforementioned sensor sheet will be explained. Here, the method for producing a sensor sheet will be described by taking the sensor sheet 2 having the structure illustrated in FIGS. 2A and 2B as an example.

(1) Two sheets of sheet-like dielectric layers formed from an elastomer composition, and two sheets of sheet-like protective layers formed from an elastomer composition are prepared. The dielectric layers and the protective layers can be produced by similar methods. Here, the production method will be explained as a method for producing the dielectric layers.

First, a raw material composition is produced by mixing an elastomer (or a raw material thereof) as a raw material composition, optionally with additives such as a chain extending agent, a crosslinking agent, a vulcanization accelerator, a catalyst, a dielectric filler, a plasticizer, an antioxidant, an age resistor, and a colorant. Next, a dielectric layer is produced by molding this raw material composition. Regarding the method for molding the raw material composition, a conventionally known technique can be employed.

Specifically, for example, in a case where a dielectric layer containing urethane elastomer is molded, the method described below or the like can be used.

First, a polyol component, a plasticizer and an antioxidant are weighed, and these components are mixed with stirring for a certain time under heating and reduced pressure to produce a mixed liquid. Next, this mixed liquid is weighed, the temperature is adjusted, subsequently a catalyst is added thereto, and the mixture is stirred with an agitator or the like. Subsequently, a predetermined amount of an isocyanate compound is added thereto, and the mixture is stirred with an agitator or the like. Subsequently, the mixed liquid is instantly poured into the forming apparatus shown in FIG. 3, the mixed liquid is produced into a sandwich form with protective films, and the mixed liquid is crosslinked and cured while being conveyed. Thus, a protective film-attached sheet having a predetermined thickness is obtained. Subsequently, if necessary, the sheet is crosslinked after a certain time, and finally, the sheet is cut into a predetermined shape. Thereby, a dielectric layer can be produced.

Figure 3:
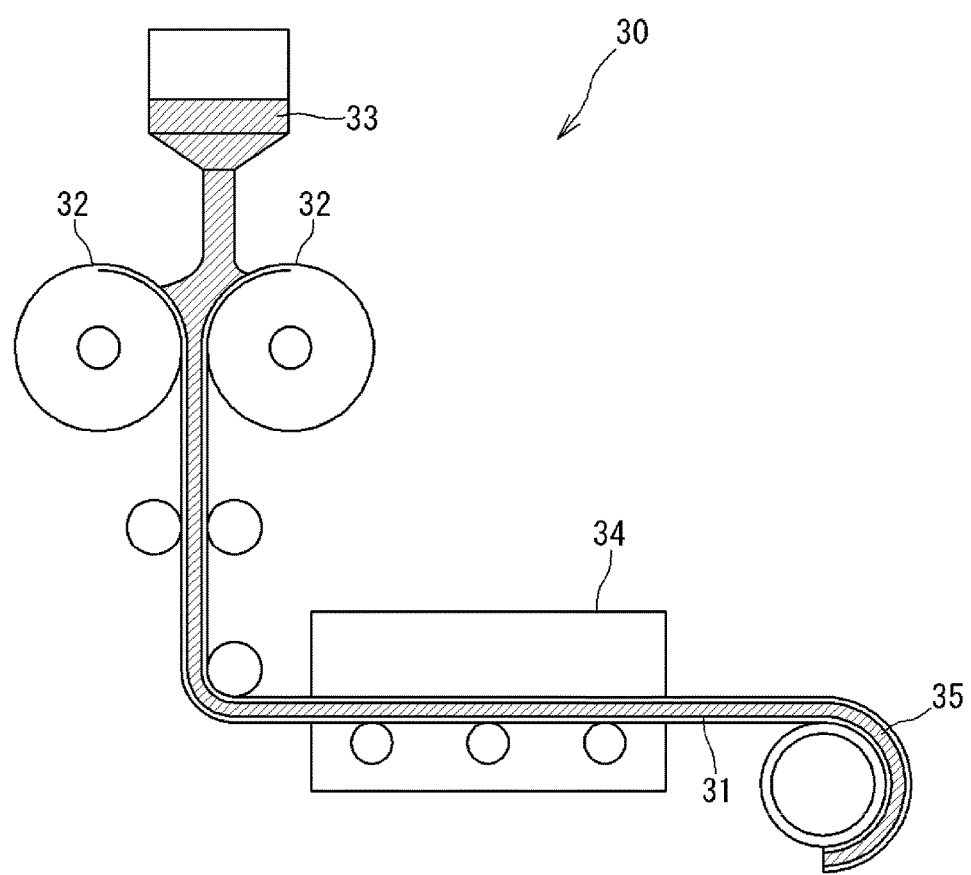
FIG. 3 is a schematic diagram for explaining an example of a forming apparatus used for the production of a dielectric layer that is included in a capacitive sensor.

FIG. 3 is a schematic diagram for explaining an example of the forming apparatus used for the production of a dielectric layer. In the forming apparatus 30 illustrated in FIG. 3, a raw material composition 33 is caused to flow into the gap of protective films 31 formed from polyethylene terephthalate (PET), which are continuously sent from a pair of rolls 32 and 32 that are disposed apart from each other, and while a curing reaction (crosslinking reaction) is carried out in a state in which the raw material composition 33 is maintained in the gap, the assembly is introduced into a heating apparatus 34. The raw material composition 33 is thermally cured in a state in which the raw material composition 33 is maintained between a pair of protective films 31, and thus a sheet-like product 35 that becomes a dielectric layer is formed.

The dielectric layer may be produced after the raw material composition is prepared, using a general-purpose film forming apparatus or a film forming method, such as various coating apparatuses, bar coating, or a doctor blade.

As described above, the protective layer may be produced by a method similar to that used for the production of the dielectric layer.

(2) Next, separately from the process of (1), an application liquid for forming an electrode layer is prepared.

Here, a composition including an electroconductive material such as carbon nanotubes and a dispersing medium is prepared as the application liquid.

Specifically, first, an electroconductive material such as carbon nanotubes is added to a dispersing medium. At this time, if necessary, the above-mentioned other components such as a binder component (or a raw material for a binder component), or a dispersant may be further added thereto.

Next, various components including an electroconductive material are dispersed (or dissolved) in the dispersing medium in a wet dispersing machine, and thereby an application liquid that is used for the formation of an electrode layer is prepared. Here, for example, dispersing may be performed using an existing dispersing machine such as an ultrasonic dispersing machine, a jet mill, or a bead mill.

Examples of the dispersing medium include toluene, methyl isobutyl ketone (MIBK), alcohols, and water. These dispersing media may be used singly, or two or more kinds thereof may be used in combination.

In regard to the application liquid, in a case where the electroconductive material is carbon nanotubes, the concentration of the carbon nanotubes is preferably 0.01% to 10% by weight. If the concentration is less than 0.01% by weight, the concentration of carbon nanotubes is too low, and it may be necessary to repeatedly apply the application liquid. On the other hand, if the concentration is more than 10% by weight, the viscosity of the application liquid becomes too high, dispersibility of the carbon nanotubes is decreased as a result of reaggregation, and it may be difficult to form a uniform electrode layer.

(3) Next, while the dielectric layer and the protective layer are superposed, and an electrode layer and the like are formed at appropriate times. Thus, a sensor sheet is produced. The present process will be explained with reference to FIG. 4A to 4D. FIGS. 4A to 4D are perspective views for explaining a production process for a sensor sheet.

Figure 4A:
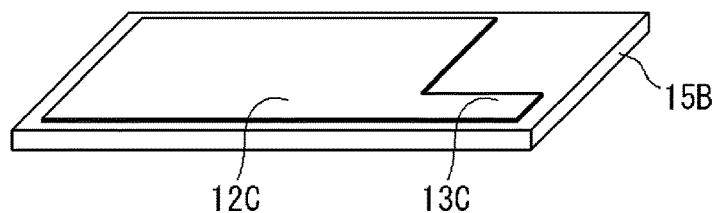
FIGS. 4A to 4D are perspective views for explaining production processes for a sensor sheet.

(a) First, at a predetermined position on one surface (top surface) of one sheet of protective layer (bottom protective layer 15B) produced in the process of (1), the application liquid prepared in the process of (2) is applied by spray coating or the like, and the application liquid is dried (see FIG. 4A). Thereby, a bottom electrode layer 12C and a bottom conducting wire 13C are formed on the bottom protective layer 15B.

Here, the drying conditions for the application liquid are not particularly limited, and the drying conditions may be appropriately selected according to the type of the dispersing medium, the composition of the elastomer composition, or the like.

Furthermore, the method for applying the application liquid is not intended to be limited to spray coating, and in addition to that, for example, a screen printing method, an inkjet printing method, and the like can also be employed.

Furthermore, when the application liquid is applied, the position at which the electrode layer is not formed is masked, and then the application liquid may be applied.

(b) Next, one sheet of dielectric layer (bottom dielectric layer 11B) produced in the process of (1) is superposed on the bottom protective layer 15B to be laminated thereon, so as to cover the entirety of the bottom electrode layer 12C and a portion of the bottom conducting wire 13C. Subsequently, a central electrode layer 12A and a central conducting wire 13A are formed at predetermined positions on the upper surface of the bottom dielectric layer 11B, using a technique similar to that of (a) (see FIG. 4B).

(c) Next, another one sheet of dielectric layer (top dielectric layer 11A) produced in the process of (1) is superposed on the bottom dielectric layer 11B to be laminated thereon, so as to cover the entirety of the central electrode layer 12A and a portion of the central conducting wire 13A. Subsequently, a top electrode layer 12B and a top conducting wire 13B are formed at predetermined positions on the upper surface of the top dielectric layer 11A, using a technique similar to that of (a) (see FIG. 4C).

(d) Next, another one sheet of protective layer (top protective layer 15A) produced in the process of (1) is laminated so as to cover the entirety of the top electrode layer 12B and a portion of the top conducting wire 13B.

Subsequently, copper foil is attached to the respective ends of the central conducting wire 13A, the top conducting wire 13B, and the bottom conducting wire 13C, and the copper foil parts are designated as a central connecting portion 14A, a top connecting portion 14B, and a bottom connecting portion 14C, respectively (see FIG. 4D).

The sensor sheet described above can be produced by employing such a method.

The sensor sheet illustrated in FIGS. 2A and 2B includes a detection portion at one site; however, according to embodiments of the present invention, the number of detection portions of the sensor sheet is not limited to one site, and the sensor sheet may include detection portions at multiple sites. Here, the first detection portion and the second detection portion are together referred to as one detection portion.

Figure 5A:
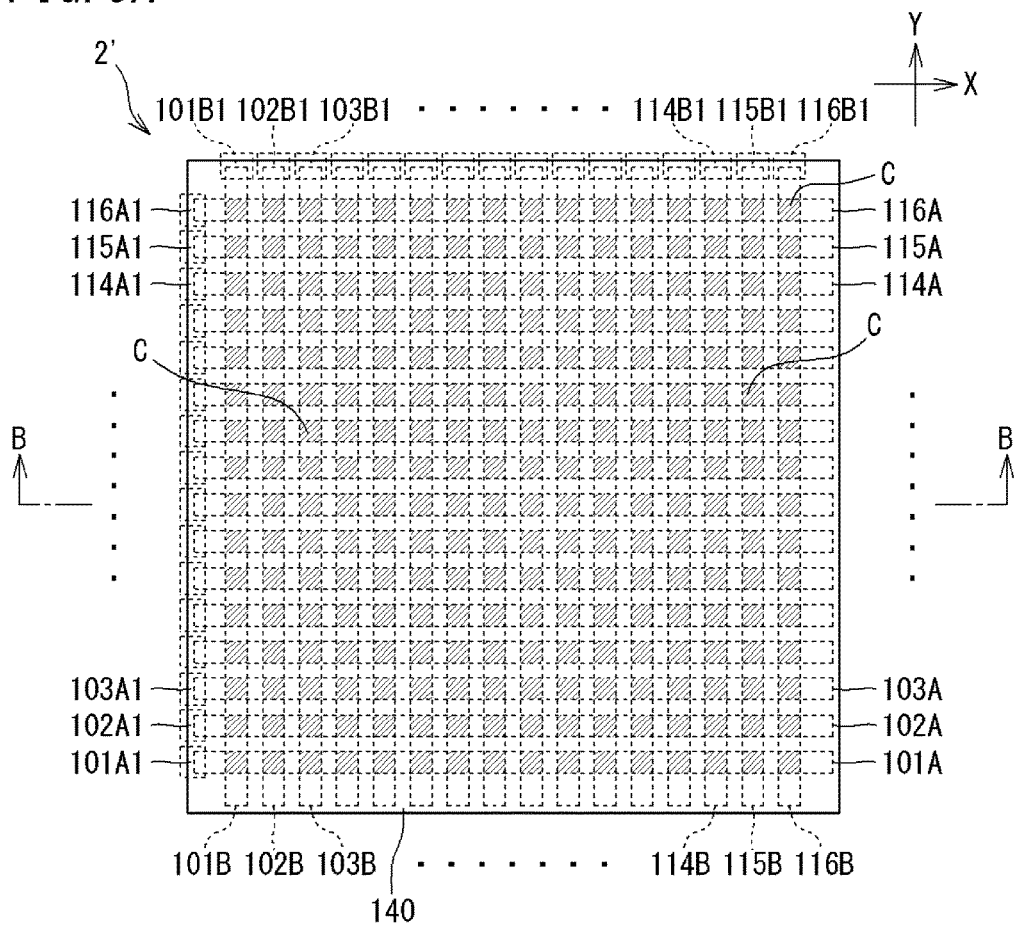
FIG. 5A is a plan view schematically illustrating another example of the sensor sheet that constitutes a capacitive sensor according to an embodiment of the present invention.
Figure 5B:
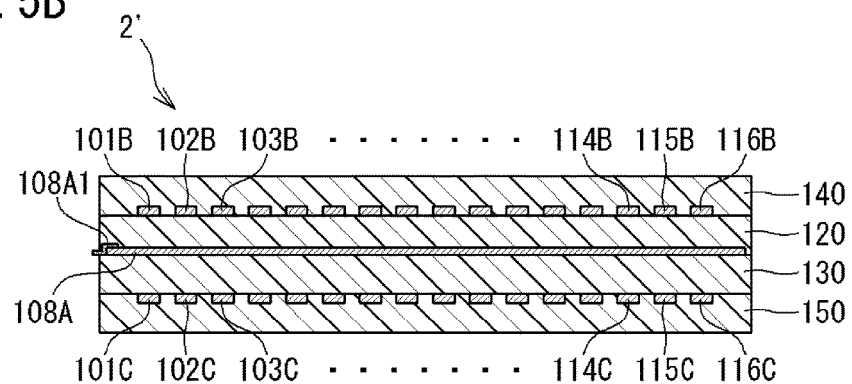
FIG. 5B is a cross-sectional view obtainable by cutting the sensor sheet along the line B-B shown in FIG. 5A.
Figure 6:
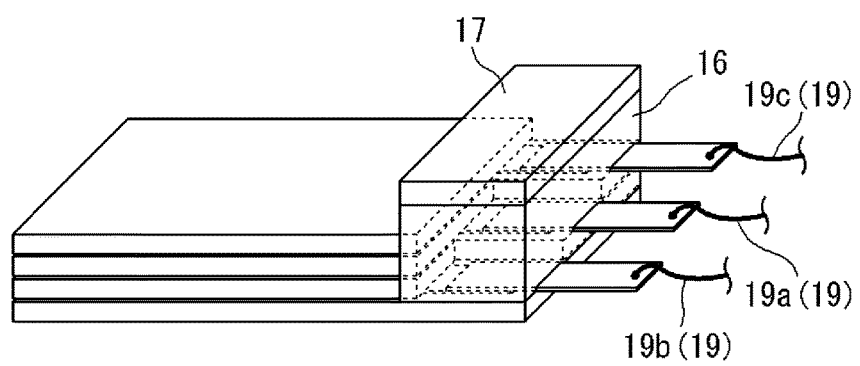
FIG. 6 is a perspective view schematically illustrating a sensor sheet A according to an Example.

Specific examples of the sensor sheet including a plurality of detection portions include, for example, a sensor sheet as illustrated in FIGS. 5A and 5B.

FIG. 5A is a plan view schematically illustrating another example of the sensor sheet that constitutes a capacitive sensor according to an embodiment of the present invention, and FIG. 5B is a cross-sectional view obtainable by cutting the sensor sheet along the line B-B shown in FIG. 5A.

As illustrated in FIGS. 5A and 5B, a sensor sheet 2' that includes a plurality of detection portions includes a sheet-like bottom dielectric layer (second dielectric layer) 130 formed from an elastomer; multiple lines of central electrode layers 101A to 116A formed on the top surface (front surface) of the bottom dielectric layer 130; multiple lines of bottom electrode layers (second outer electrode layers) 101C to 116C formed on the bottom surface of the bottom dielectric layer 130; a top dielectric layer (first dielectric layer) 120 laminated on the top side (in FIG. 5B, upper side) of the central electrode layers 101A to 116A; and multiple lines of top electrode layers (first outer electrode layers) 101B to 116B formed on the top surface of the top dielectric layer 120.

Furthermore, the sensor sheet 2' includes connecting portions (in FIG. 5A, 101A1 to 116A1, 101B1 to 116B1, and the like) to be each connected to an external conducting wire mounted at one end of each of the central electrode layers 101A to 116A, the bottom electrode layers 101C to 116C, and the top electrode layers 101B to 116B.

Furthermore, in the sensor sheet 2', a top protective layer (first protective layer) 140 is provided on the top side of the top dielectric layer 120, and a bottom protective layer (second protective layer) 150 is provided on the bottom side of the bottom dielectric layer 130.

The central electrode layers 101A to 116A each have a rectangle shape, and the sensor sheet 2' has 16 central electrode layers in total.

The central electrode layers 101A to 116A are respectively extended in the X-direction (in FIG. 5A, horizontal direction). The central electrode layers 101A to 116A are separated apart at a predetermined interval in the Y-direction (in FIG. 5A, vertical direction) and are respectively disposed so as to be approximately parallel to each other.

The top electrode layers 101B to 116B each have a rectangle shape, and the sensor sheet 2' has 16 top electrode layers in total.

The top electrode layers 101B to 116B are respectively disposed so as to intersect approximately orthogonally with the central electrode layers 101A to 116A as viewed from the top-bottom direction (thickness direction of the dielectric layer). That is, the top electrode layers 101B to 116B are respectively extended in the Y-direction. Furthermore, the top electrode layers 101B to 116B are separated apart at a predetermined interval in the X-direction and are respectively disposed so as to be approximately parallel to each other.

The bottom electrode layers 101C to 116C each have a rectangle shape, and the sensor sheet 2' has 16 bottom electrode layers in total.

The bottom electrode layers 101C to 116C are respectively disposed so as to overlap with the top electrode layers 101B to 116B as viewed from the top-bottom direction. Therefore, the bottom electrode layers 101C to 116C are disposed so as to intersect approximately orthogonally with the central electrode layers 101A to 116A as viewed from the top-bottom direction.

In the sensor sheet 2', as viewed from the top-bottom direction, the respective sites where the central electrode layers 101A to 116A, the top electrode layers 101B to 116B, and the bottom electrode layers 101C to 116C face each other (as shown in FIG. 5A, 256 sites in sensor sheet 2') become detection portions C.

Regarding the various detection portions C, the part where a central electrode layer and a top electrode layer face each other becomes a top detection portion (first detection portion), and the part where a central electrode layer and a bottom electrode layer face each other becomes a bottom detection portion (second detection portion).

In a capacitive sensor including the sensor sheet 2', the capacitance of each detection portion can be measured by changing the detection portions C at 256 sites one by one, and as a result, the amount of strain at each detection portion or the positional information for strain within a capacitive sensor sheet can be detected.

<Measuring Instrument>

The measuring instrument is electrically connected to the sensor sheet. The measuring instrument has a function of measuring capacitance of the detection portions (first detection portion and second detection portion), which changes with deformation of the dielectric layer.

At this time, the structure of the detection portions of the sensor sheet (structure of the first detection portion and the second detection portion) is regarded as a structure in which two condensers are arranged in parallel, the top electrode layer (top connecting portion) and the bottom electrode layer (bottom connecting portion) are connected to the same terminal of the measuring instrument, and the central electrode layer (central connecting portion) is connected to a terminal that is different from the terminal to which the top electrode layer and the bottom electrode layer are connected. Thus, capacitance is measured.

In addition, in a case where the sensor sheet includes multiple detection portions as in the case of the sensor sheet 2' illustrated in FIGS. 5A and 5B, measurement of capacitance of the detection portion that is an object of measurement is performed in a state in which a central electrode layer other than the central electrode layer (central connecting portion) positioned at the detection portion as the object of measurement is grounded.

Therefore, in regard to the capacitive sensor sheet, the capacitance of the detection portion is measured as the total capacitance Ct (Ct=C1+C2) obtainable by adding the capacitance C1 of the first detection portion and the capacitance C2 of the second detection portion. In the capacitive sensor sheet, the state of deformation of the sensor sheet is measured on the basis of this total capacitance Ct.

That is, in the capacitive sensor, it is preferable that a state in which the top electrode layer and the bottom electrode layer are electrically connected (state of being short-circuited) is established, and the respective capacitances of the first detection portion and the second detection portion are measured in this state. Thereby, the change in capacitance can be measured more accurately.

Here, the technique of electrically connecting the top electrode layer and the bottom electrode layer is not particularly limited, and for example, the following technique can be employed. That is, (1) a technique of electrically connecting the two (top electrode layer and bottom electrode layer) within the sensor sheet (for example, a conducting wire that connects the top conducting wire and the bottom conducting wire is formed); (2) a technique of connecting the two between the sensor sheet and a measuring instrument (for example, an external conducting wire connected to the top conducting wire and an external conducting wire connected to the bottom conducting wire are connected and then are connected to a measuring instrument); (3) a technique of connecting the two within a measuring instrument (for example, in a capacitance measuring circuit); and the like can be employed.

The method for measuring the capacitance Ct is not particularly limited; however, a method of using alternating current impedance is preferred. The measurement method using alternating current impedance has excellent repetition accuracy even upon measurement using a high frequency signal, and since a high frequency signal is used, the impedance value does not become too large. Thus, the measurement accuracy can be further increased. Also, since the time required for measurement of capacitance can be shortened, it is possible for a sensor to have an increased number of times of measurement per time.

The measuring instrument includes a capacitance measuring circuit needed for the measurement of capacitance, an arithmetic circuit, an amplifier circuit, a power supply circuit, and the like.

A specific example of the method for measuring the capacitance Ct (circuit) is not limited to the method of using in combination the Schmitt trigger oscillator circuit and the F/V conversion circuit that are shown in FIG. 1. For example, a CV conversion circuit utilizing an auto-balancing bridge circuit (LCR meter or the like), a CV conversion circuit utilizing an inverting amplifier circuit, a CV conversion circuit utilizing a half-wave voltage doubler rectifier circuit, and a CF oscillator circuit utilizing a Schmitt trigger oscillator circuit may also be employed.

Here, in order to measure the capacitance of a detection portion more accurately, in a case where (1) the measuring instrument includes a CF conversion circuit such as a Schmitt trigger oscillator circuit, it is preferable that the central electrode layer is electrically connected to the CF conversion circuit side and the top electrode layer and the bottom electrode layer are grounded in a state in which the top electrode layer and the bottom electrode layer are electrically connected. Furthermore, in a case where (2) the measuring instrument includes a half-wave voltage doubler rectifier circuit, an inverting amplifier circuit or an auto-balancing bridge circuit, it is preferable that the central electrode layer is electrically connected to the half-wave voltage doubler rectifier circuit, inverting amplifier circuit or auto-balancing bridge circuit side, and the top electrode layer and the bottom electrode layer are electrically connected to the alternating current signal generation side of the measuring instrument in a state in which the top electrode layer and the bottom electrode layer are electrically connected.

Furthermore, in a case where the sensor sheet includes multiple detection portions as in the case of the sensor sheet 2' illustrated in FIGS. 5A and 5B, it is preferable to measure the capacitance of a detection portion that is an object of measurement, while changing the circuit so as to attain the following connection state (1) or (2).

That is, (1) In a Case in which the Measuring Instrument Includes a CF Conversion Circuit Such as a Schmitt Trigger Oscillator Circuit:

A central electrode layer located in a detection portion that is an object of measurement is electrically connected to the CF conversion circuit side, and another central electrode layer is grounded. Furthermore, the top electrode layers and the bottom electrode layers that face each other in the top-bottom direction are respectively electrically connected, and a pair of a top electrode layer and a bottom electrode layer that is located, in a state of being electrically connected to each other, at a detection portion as an object of measurement, is grounded.

(2) In a Case in which the Measuring Instrument Includes a Half-Wave Voltage Doubler Rectifier Circuit, an Inverting Amplifier Circuit or an Auto-Balancing Bridge Circuit:

A central electrode layer located in a detection portion that is an object of measurement is electrically connected to the half-wave voltage doubler rectifier circuit, inverting amplifier circuit or auto-balancing bridge circuit side, and another central electrode layer is grounded. Furthermore, while the top electrode layers and the bottom electrode layers that face each other in the top-bottom direction are respectively electrically connected, a pair of a top electrode layer and a bottom electrode layer that is located, in a state of being electrically connected to each other, at a detection portion as an object of measurement, is electrically connected to the alternating current signal generation side of the measuring instrument.

Meanwhile, according to the embodiments of the present invention, the term grounding is a concept including not only a case in which the electrode layer is earthed, but also a case in which the electrode layer is fixed at a predetermined potential (for example, 0 V).

In a case in which various electrode layers are grounded, for example, the electrode layers may be connected to a GND terminal or the like of a measuring instrument.

<Display Device>

The capacitive sensor may include a display device as in the case of the example shown in FIG. 1. Thereby, a user of the capacitive sensor can check the information based on the change of capacitance Ct in real time. The display device includes a monitor, an arithmetic circuit, an amplifier circuit, a power supply circuit and the like, which are needed for that purpose.

Furthermore, in order to store the measurement results for capacitance Ct as in the case of the example shown in FIG. 1, the display device may also include a memory unit such as RAM, ROM, or HDD. Meanwhile, the memory unit may also be included in the measuring instrument.

Regarding the display device, terminal equipment such as a personal computer, a smart phone, or a tablet may also be utilized.

Furthermore, in regard to the capacitive sensor 1 shown in FIG. 1, connection between the measuring instrument 3 and the display device 4 is wired; however, the connection thereof in the capacitive sensor is not necessarily required to be wired, and wireless connection is also acceptable. According to the use embodiment of the capacitive sensor, it may be easier to use a sensor in which the measuring instrument and the display device are physically separated.

The capacitive sensor according to embodiments of the present invention can determine the amount of deformation of a sensor sheet at the time of deformation, by measuring the capacitances (total capacitance Ct of the first detection portion and the second detection portion) before and after deformation when the dielectric layers (top dielectric layer and bottom dielectric layer) of the sensor sheet are deformed, and calculating the amount of change of total capacitance Ct before and after deformation, ΔCt, from the measurement results. Therefore, the capacitive sensor can be used, for example, as a sensor for determining the amount of deformation of a measuring object.

In a case in which the sensor sheet includes multiple detection portions, the capacitive sensor may also be used as a sensor for determining the deformation strain distribution of a measuring object.

The capacitive sensor can be used, for example, as a sensor for measuring deformation of a measuring object by taking a stretchable product such as an expander, a rehabilitation tube, a rubber ball, a rubber balloon or an airbag, or a flexible product such as a cushion or an innersole, as a measuring object, and attaching the sensor sheet to this measuring object.

The capacitive sensor can be used, for example, as a sensor which is intended for an animal such as a human being as a measuring object, and measures the motion of the measuring object. Specifically, for example, when the sensor sheet is used by being attached to any arbitrary site on the surface of the body, such as a joint; a place where a pulse is felt, such as a radial artery or a carotid artery; the palm or the bottom of the hand; the sole or the top of the foot; the chest or abdomen; or around the cheek or the mouth, the capacitive sensor can be used as a sensor for measuring deformation (motion) at the surface of the body.

Furthermore, regarding the capacitive sensor, for example, when a person wears clothes, and the sensor sheet is used by being attached to the surface of the clothes, the capacitive sensor can be used as a sensor for measuring the mode of deformation (stretch) of clothes in accordance with the motion of the body, or followability of the clothes to the body.

Furthermore, in the capacitive sensor, for example, the user may actively change the shape of the sensor sheet. In that case, the capacitive sensor can also be used for a user interface apparatus which produces information that reflects the intention of the user on the basis of the change in capacitance, and transmits the information.

Furthermore, in regard to the capacitive sensor described above, the sensor sheet can be utilized as a substitute for the interface of a myoelectric sensor for electric artificial arm or legs.

Also, in the capacitive sensor described above, the sensor sheet can also be used as an input terminal for the input interface for severe psychosomatic disabled people.

In regard to the capacitive sensor described above, in a case where the sensor sheet includes a large number of detection portions, the capacitive sensor can be used as a sensor for detecting the positional information obtainable when a measuring object is moved in a state of being contacted with the sensor sheet. Furthermore, for example, the capacitive sensor can also be used for the input interface for touch panels.

Meanwhile, the capacitive sensor described above can also be utilized for measurement at a light-shielded site where measurement cannot be made with an existing sensor utilizing optical motion capture.

As such, the capacitive sensor according to the embodiments of the present invention can be used in various fields of utilization and use environments. As described above, the capacitive sensor comes to be exposed to various measurement noises, such as electronic noise, power supply noise, and the contact of one surface or both surfaces of a sensor sheet with an electric conductor (for example, the body or sweat), in each field of utilization or use environment.

In this regard, the capacitive sensor can suppress the fluctuation in the measured value of capacitance to a low level, even if the noise situation around the capacitive sensor changes at the time of measuring capacitance.

EXAMPLES

Hereinafter, embodiments of the present invention will be more specifically described by way of Examples; however, the embodiments of the present invention are not intended to be limited to the following Examples.

<Production of Sensor Sheet A>

(1) Production of Dielectric Layers (Top Dielectric Layer and Bottom Dielectric Layer)

To 100 parts by mass of a polyol (PANDEX GCB-41, manufactured by DIC Corp.), 40 parts by weight of a plasticizer (dioctyl sulfonate) and 17.62 parts by weight of an isocyanate (PANDEX GCA-11, manufactured by DIC Corp.) were added, and the mixture was mixed with stirring for 90 seconds using an agitator. Thus, a raw material composition for a dielectric layer was prepared. Next, the raw material composition was poured into a forming apparatus 30 such as shown in FIG. 3, and the raw material composition was produced into a sandwich form with protective films 31. While the assembly was conveyed, the raw material composition was cured by crosslinking under the conditions of a furnace internal temperature of 70° C. and a furnace retention time of 30 minutes, and thus a rolled sheet having protective films attached thereto and having a predetermined thickness was obtained. Subsequently, the rolled sheet was kept for 12 hours in a furnace that had been adjusted to 70° C. and then was crosslinked. Thus, a sheet formed from polyether-based urethane elastomer was produced. The urethane sheet thus obtained was cut, and two sheets of a sheet having a size of 14 mm×74 mm×50 μm in thickness were produced. Furthermore, one place of a corner part was cut out from one sheet of the cut sheet into a size of 5 mm×7 mm×50 μm in thickness, and thus a top dielectric layer was produced. Furthermore, one place of a corner part was cut out from the other sheet of the cut sheet into a size of 9 mm×7 mm×50 μm in thickness, and thus a bottom dielectric layer was produced.

For the dielectric layers thus produced, the elongation at break (%) and the relative permittivity were measured. The elongation at break (%) was 505%, and the relative permittivity was 5.7.

Here, the elongation at break was measured according to JIS K 6251.

Regarding the relative permittivity, a dielectric layer was interposed between electrodes having a diameter of 20 mmφ, and capacitance was measured at a measurement frequency of 1 kHz using a LCR HITESTER (manufactured by Hioki E.E. Corp., 3522-50). Thus, the relative permittivity was calculated from the electrode area and the thickness of the measurement sample.

(2) Production of Electrode Layer Material 30 mg of highly oriented carbon nanotubes manufactured by Taiyo Nippon Sanso Corp. (number of layers: 4 to 12 layers, fiber length: 5 to 20 nm, fiber length: 150 to 300 μm, and carbon purity: 99.5%), which were multi-walled carbon nanotubes produced by a substrate growth method, was added to 30 g of 2-propanol, and the mixture was subjected to a wet dispersing treatment using a jet mill (NANO JET PUL JN10-SP003, manufactured by JOKOH CO., LTD.). The dispersion was diluted to 10 times, and thus a carbon nanotube dispersion liquid having a concentration of 0.01% by weight was obtained.

(3) Production of Protective Layers (Top Protective Layer and Bottom Protective Layer)

A bottom protective layer having a size of 14 mm×74 mm×50 μm in thickness, and a top protective layer having a size of 14 mm×67 mm×50 μm in thickness were produced from polyether-based urethane elastomer, using a method similar to that used in section (1) Production of dielectric layers.

(4) Production of Sensor Sheet A

A sensor sheet was produced through the production process described below (see FIGS. 4A to 4D and FIG. 6).

(a) A mask produced by forming an opening having a predetermined shape in a release-treated PET film (not shown in the diagram), was attached to one surface (top surface) of the bottom protective layer 15B produced in the process of (3).

In the mask, an opening corresponding to the position of the bottom electrode layer and the bottom conducting wire is formed, and the size of the opening is such that the portion corresponding to the bottom electrode layer has a size of 10 mm in width×50 mm in length, and the portion corresponding to the bottom conducting wire has a size of 2 mm in width×10 mm in length.

Next, 7.2 g of the carbon nanotube dispersion liquid produced in the process of (2) was applied thereon from a distance of 10 cm using an airbrush, and subsequently the dispersion liquid was dried for 10 minutes at 100° C. Thus, a bottom electrode layer 12C and a bottom conducting wire 13C were formed. Subsequently, the mask was detached (see FIG. 4A).

(b) Next, the bottom dielectric layer 11B produced in the process of (1) was laminated on the bottom protective layer 15B by superposing the bottom dielectric layer 11B thereon so as to cover the entirety of the bottom electrode layer 12C and a portion of the bottom conducting wire 13C.

Figure 4B:
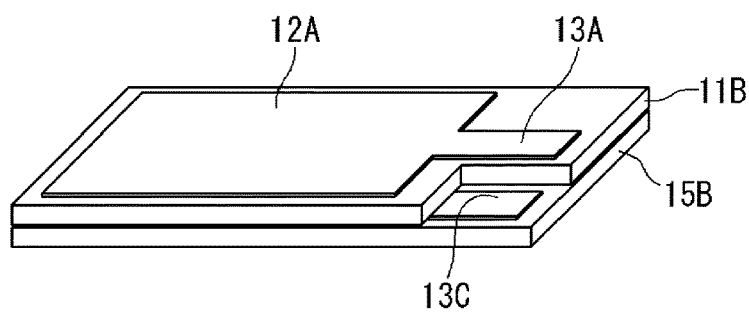

Furthermore, on the top side of the bottom dielectric layer 11B, a central electrode layer 12A and a central conducting wire 13A were formed at a predetermined position (position at which the bottom electrode layer 12C and the central electrode layer 12A overlapped in a planar view), using a technique similar to that used for the formation of the bottom electrode layer 12C and the bottom conducting wire 13C in Step (a) (see FIG. 4B).

(c) Next, the top dielectric layer 11A produced in the process of (1) was laminated on the bottom dielectric layer 11B by superposing the top dielectric layer 11A thereon so as to cover the entirety of the central electrode layer 12A and a portion of the central conducting wire 13A.

Figure 4C:
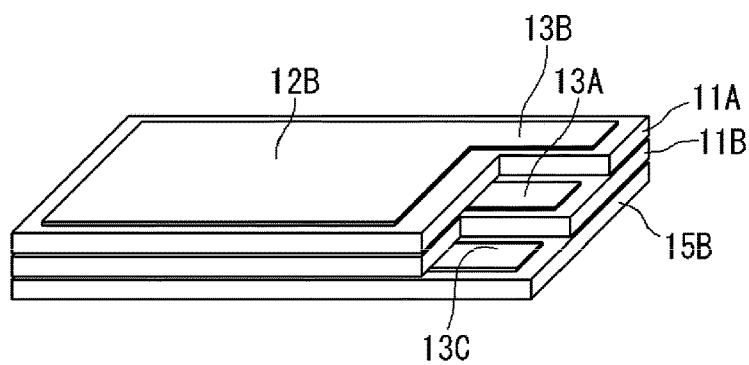

Furthermore, on the top side of the top dielectric layer 11A, a top electrode layer 12B and a top conducting wire 13B were formed at a predetermined position (position at which the central electrode layer 12A and the top electrode layer 12B overlapped in a planar view), using a technique similar to that used for the formation of the bottom electrode layer 12C and the bottom conducting wire 13C in Step (a) (see FIG. 4C).

Figure 4D:
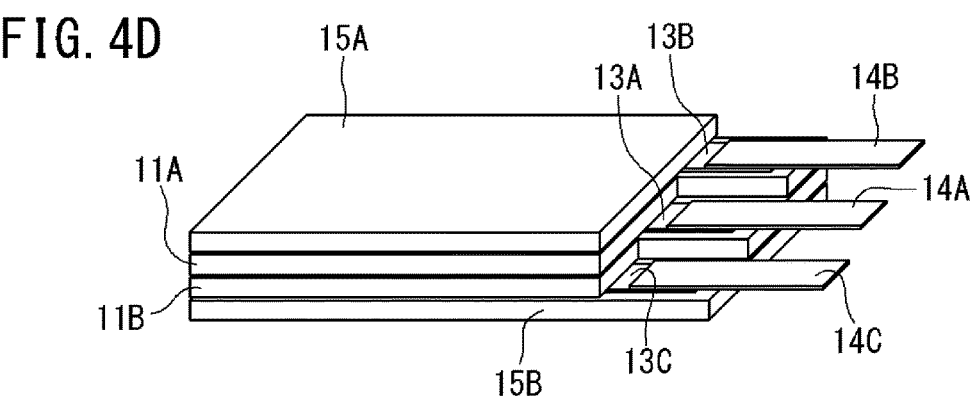

(d) Next, the top protective layer 15A produced in the process of (3) was laminated on the top side of the top dielectric layer 11A where the top electrode layer 12B and the top conducting wire 13B had been formed, so as to cover the entirety of the top electrode layer 12B and a portion of the top conducting wire 13B (see FIG. 4D).

(e) Subsequently, copper foil was attached to the respective ends of the central conducting wire 13A, the top conducting wire 13B and the bottom conducting wire 13C, and these were designated as a central connecting portion 14A, a top connecting portion 14B and a bottom connecting portion 14C, respectively.

Next, lead wires 19 (19a to 19c) that served as external conducting wires were fixed by soldering to the central connecting portion 14A, the top connecting portion 14B and the bottom connecting portion 14C, respectively.

Furthermore, a PET film 17 having a thickness of 100 μm was attached for reinforcement by means of an acrylic pressure-sensitive tape (manufactured by 3M Company, Y-4905 (thickness 0.5 mm)) 16, to the portion positioned on the bottom protective layer 15B of the central connecting portion 14A, the top connecting portion 14B and the bottom connecting portion 14C. Thus, a sensor sheet A was completed (see FIG. 6).

The sensor sheet A includes a central electrode layer; a top dielectric layer and a bottom dielectric layer formed so as to sandwich the central electrode layer therebetween; and a top electrode layer and a bottom electrode layer formed on the reverse sides of the top dielectric layer and the bottom dielectric layer.

<Production of Sensor Sheet B>

(1) Production of Dielectric Layer

A polyether-based urethane elastomer sheet having a size of 14 mm×74 mm×50 µm in thickness was produced in the same manner as in the case of the production of sensor sheet A, and then one place of a corner part was cut out into a size of 7 mm×7 mm×50 µm in thickness. Thus, a dielectric layer was produced.

(2) Production of Electrode Layer Material

A carbon nanotube dispersion liquid was produced in the same manner as in the case of the production of sensor sheet A.

(3) Production of Protective Layers (Top Protective Layer and Bottom Protective Layer)

A bottom protective layer having a size of 14 mm×74 mm×50 µm in thickness and a top protective layer having a size of 14 mm×67 mm×50 µm in thickness were produced from polyether-based urethane elastomer, in the same manner as in the case of the production of sensor sheet A.

Figure 7:
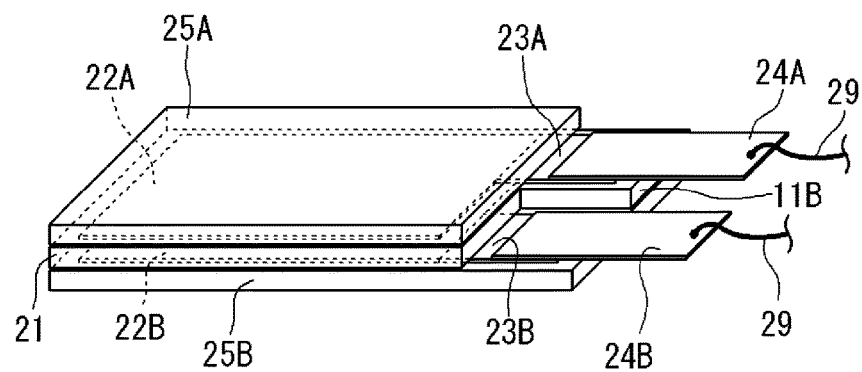
FIG. 7 is a perspective view schematically illustrating a sensor sheet B according to a Comparative Example.

(4) Production of Sensor Sheet B (See FIG. 7)

(a) A mask produced by forming an opening having a predetermined shape in a release-treated PET film was attached to one surface (top surface) of the bottom protective layer 25B produced in the process of (3), and then the carbon nanotube dispersion liquid prepared in the process of (2) was applied thereon using an airbrush and dried. Subsequently, the mask was detached, and thereby a bottom electrode layer 22B and a bottom conducting wire 23B were formed.

Regarding a specific method for the present process, a method similar to that used in step (a) of (4) for the production of sensor sheet A was employed. However, regarding the size of the opening in the mask, the portion corresponding to the bottom electrode layer had a size of 10 mm in width×50 mm in length, and the portion corresponding to the bottom conducting wire had a size of 2 mm in width×10 mm in length.

(b) Next, the dielectric layer 21 produced in the process of (1) was laminated on the bottom protective layer 25B by superposing the dielectric layer 21 so as to cover the entirety of the bottom electrode layer 22B and a portion of the bottom conducting wire 23B.

Furthermore, on the top side of the dielectric layer 21, a top electrode layer 22A and a top conducting wire 23A were formed at a predetermined position (position at which the bottom electrode layer 22B and the top electrode layer 22A overlapped in a planar view), using a technique similar to that used for the formation of the bottom electrode layer 22B and the bottom conducting wire 23B in Step (a).

(c) Next, on the top side of the dielectric layer 21 where the top electrode layer 22A and the top conducting wire 23A had been formed, the top protective layer 25A produced in the process of (3) was laminated so as to cover the entirety of the top electrode layer 22A and a portion of the top conducting wire 23A.

(d) Subsequently, copper foil was attached to the respective ends of the top conducting wire 23A and the bottom conducting wire 23B, and these were designated as a top connecting portion 24A and a bottom connecting portion 24B, respectively. Subsequently, lead wires 29 that served as external conducting wires were fixed by soldering to the top connecting portion 24A and the bottom connecting portion 24B (see FIG. 7).

Finally, a PET film having a thickness of 100 µm was attached for reinforcement by means of an acrylic pressure-sensitive tape (manufactured by 3M Company, Y-4905 (thickness 0.5 mm)), to the portion positioned on the bottom protective layer 25B of the top connecting portion 24A and the bottom connecting portion 24B in the same manner as in the case of the production of sensor sheet A. Thus, a sensor sheet B was completed.

The sensor sheet B includes a single dielectric layer and electrode layers formed on both surfaces thereof.

<Confirmation of Initial Performance of Sensor Sheets A and B>

Sensor sheet A and sensor sheet B produced by the method described above were respectively connected to a LCR meter (manufactured by Hioki E.E. Corp., LCR HITESTER 3522-50) by means of lead wires as described below, and the capacitance was measured in an unelongated state. The results are presented in Table 1.

(Connection State)

A: Sensor sheet A and a LCR meter were connected. At this time, the central electrode layer and the bottom electrode layer were respectively connected to different terminals of the LCR meter, and the top electrode layer was not connected to the LCR meter. That is, the lead wires 19a and 19b shown in FIG. 6 were separately connected to the LCR meter, and the lead wire 19c was not connected to the LCR meter.

B: Sensor sheet A and a LCR meter were connected. At this time, the top electrode layer and the bottom electrode layer were electrically connected (in a state in which the top electrode layer and the bottom electrode layer were short-circuited), and this was connected to the LCR meter. The central electrode layer was connected to a terminal of the LCR meter that was different from the terminal to which the top electrode layer and the bottom electrode layer were connected. That is, the lead wires 19b and 19c shown in FIG. 6 were gathered into one lead wire, and this was connected to the LCR meter. Also, the lead wire 19a was connected to another terminal of the LCR meter.

C: Sensor sheet B and a LCR meter were connected. At this time, the top electrode layer and the bottom electrode layer were respectively connected to different terminals of the LCR meter.

TABLE 1

| Sensor sheet | Connection state | Frequency (Hz) | Capacitance (pF) |
|---|---|---|---|
| Sensor sheet B | C | 100000 | 251.4 |
| | | 50000 | 251.8 |
| | | 20000 | 252.2 |
| | | 10000 | 252.0 |
| | | 5000 | 252.7 |
| | | 2000 | 252.4 |
| | | 1000 | 252.7 |
| Sensor sheet A | A | 100000 | 254.3 |
| | | 50000 | 255.3 |
| | | 20000 | 256.0 |
| | | 10000 | 255.9 |
| | | 5000 | 256.3 |
| | | 2000 | 256.3 |
| | | 1000 | 256.4 |
| | B | 100000 | 496.7 |
| | | 50000 | 499.9 |
| | | 20000 | 501.5 |

TABLE 1-continued

| Sensor sheet | Connection state | Frequency (Hz) | Capacitance (pF) |
|---|---|---|---|
| | | 10000 | 501.6 |
| | | 5000 | 501.7 |
| | | 2000 | 501.8 |
| | | 1000 | 502.2 |

As shown in Table 1, in regard to the sensor sheet A, the top electrode layer and the bottom electrode layer are electrically connected by a lead wire (in a state in which the top electrode layer and the bottom electrode layer are short-circuited), this lead wire is connected to one terminal of a LCR meter, and the central electrode layer is connected to another terminal through a lead wire. Thus, the total capacitance Ct of the capacitance C1 of the first detection portion and the capacitance C2 of the second detection portion of the sensor sheet A can be measured.

It became clear that the total capacitance Ct was about two times the capacitance C2 of the second detection portion. Meanwhile, it is speculated that the reason why the total capacitance Ct was not exactly two times the capacitance C2 was based on the dimensional error of the various electrode layers.

Relation Between Capacitive Sensor and Noise:
Examples 1 to 3 and Comparative Examples 1 to 3

Here, a sensor sheet and a measuring instrument were connected in any one state selected from (i) a state in which a noise source is not installed on both sides of the sensor sheet, (ii) a state in which a noise source is installed on only one side of the sensor sheet, and (iii) a state in which noise sources are installed on both sides of the sensor sheet. Thus, the capacitances of the detection portions of various sensor sheets were measured.

At this time, a DC power supply (constant voltage power supply) was used as the power supply of the measuring instrument, and in order to avoid any influence exerted by noise penetrating from earth to a DC power supply and a function generator, which is a noise source, AC supplied from the same AC wall socket was used.

Here, in the case of (i) and (ii) described above, first, copper foil was placed on a working bench made of polypropylene, and the sensor sheet was placed on this copper foil such that the bottom side of the sensor sheet faced the copper foil, and no air bubbles would remain between the copper foil and the sensor sheet. Subsequently, a function generator (manufactured by Tektronix, Inc., AFG3021) was connected to the copper foil.

In the case of (ii), a predetermined noise signal (60 Hz, −2.5 V to 2.5 V, or 10 kHz, −1.0 V to 1.0 V) was applied to the copper foil.

On the other hand, in the case of (i), the process was carried out with the function generator in an OFF state.

In the case of (iii), similarly to the case of (ii), the sensor sheet was placed on the copper foil such that no air bubbles remained between the two, and then a brass plate having a thickness of 1 mm was mounted on the upper surface of the sensor sheet. Subsequently, a function generator (AFG3021) was connected to the copper foil and the brass plate, and a predetermined noise signal (60 Hz, −2.5 V to 2.5 V, or 10 kHz, −1.0 V to 1.0 V) was applied respectively to the copper foil and the brass plate.

Example 1

Figure 8:
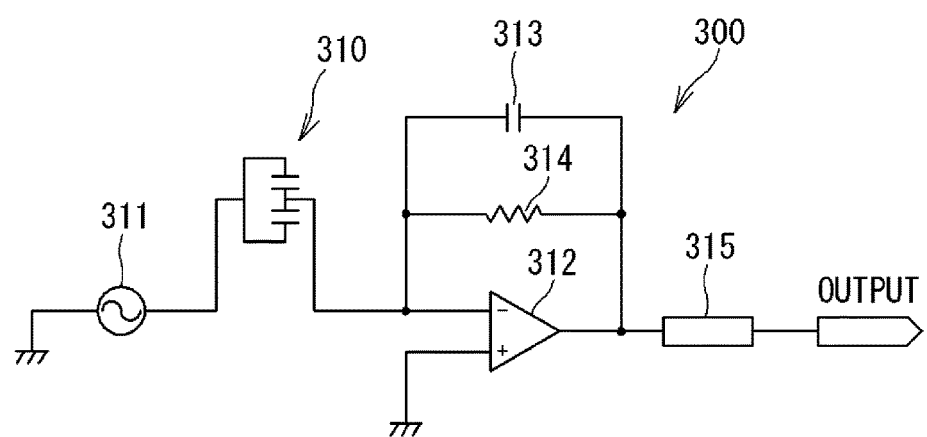
FIG. 8 is a schematic diagram illustrating an inverting amplifier circuit used for the measurement of capacitance in Example 1 and Comparative Example 1.

An inverting amplifier circuit 300 as illustrated in FIG. 8 was used as a measuring instrument, this was connected to the sensor sheet A (in FIG. 8, 310), and the total capacitance Ct was measured. For the inverting amplifier circuit 300, the oscillation frequency of an alternating current impression apparatus 311 was set to 5 kHz, the capacitance of a feedback capacitor 313 was set to 1,000 pF, and the resistance value of feedback resister 314 was set to 4.7 MΩ. In FIG. 8, reference numeral 315 represents a BEF (band elimination filter).

In this case, the wiring condition in which the central electrode layer was connected to an arithmetic amplifier 312, and the top electrode layer and the bottom electrode layer were connected, in a state of being short-circuited, to the alternating current impression apparatus 311, was designated as proper connection. In contrast, the wiring condition in which the central electrode layer was connected to the alternating current impression apparatus 311, and the top electrode layer and the bottom electrode layer were connected, in a state of being short-circuited, to the arithmetic amplifier 312, was designated as reverse connection. For the respective wiring conditions, measurement was made in a noise state of the cases (i) to (iii). The results are presented in Table 2.

Meanwhile, in regard to the explanation on the method for connecting the electrode layers in the various Examples, a state in which electrode layers are short-circuited means that the electrode layers are in a state of being electrically connected.

Comparative Example 1

An inverting amplifier circuit 300 similar to that used in Example 1 was used as a measuring instrument, this was connected to the sensor sheet B, and the capacitance of the detection portion was measured.

At this time, the wiring condition in which the top electrode layer was connected to an arithmetic amplifier 312, and the bottom electrode layer was connected to an alternating current impression apparatus 311, was designated as proper connection. In contrast, the wiring condition in which the top electrode layer was connected to the alternating current impression apparatus 311, and the bottom electrode layer was connected to the arithmetic amplifier 312, was designated as reverse connection. For the respective wiring conditions, measurement was made in a noise state of the case (i) or (ii). The results are presented in Table 2.

Example 2

Figure 9:
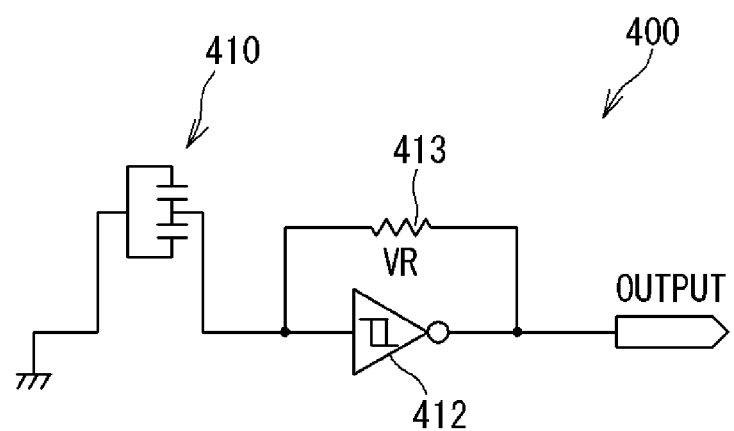
FIG. 9 is a schematic diagram illustrating a Schmitt trigger oscillator circuit used for the measurement of capacitance in Example 2 and Comparative Example 2.

A Schmitt trigger oscillator circuit 400 as illustrated in FIG. 9 was used as a measuring instrument, this was connected to the sensor sheet A (in FIG. 9, 410), and the total capacitance Ct based on the output frequency from a Schmitt trigger 412 was measured. For the Schmitt trigger oscillator circuit 400, the resistance value of a variable resister 413 was regulated such that the oscillation frequency for proper connection in conventional measurement would be 5 kHz.

At this time, the wiring condition in which the central electrode layer was connected to the Schmitt trigger 412 side, and the top electrode layer and the bottom electrode layer were grounded in a state of being short-circuited, was designated as proper connection. In contrast, the wiring condition in which the central electrode layer was grounded, and the top electrode layer and the bottom electrode layer were connected, in a state of being short-circuited, to the Schmitt trigger 412 side, was designated as reverse connection. For the respective wiring conditions, measurement was made in a noise state of the cases (i) to (iii). The results are presented in Table 2.

Comparative Example 2

A Schmitt trigger oscillator circuit 400 similar to that used in Example 2 was used as a measuring instrument, this was connected to the sensor sheet B, and the capacitance of the detection portion was measured.

At this time, the wiring condition in which the top electrode layer was connected to the Schmitt trigger 412 side, and the bottom electrode layer was grounded, was designated as proper connection. In contrast, the wiring condition in which the top electrode layer was grounded, and the bottom electrode layer was connected to the Schmitt trigger 412 side, was designated as reverse connection. For the various wiring conditions, measurement was made in a noise state of the case (i) or (ii). The results are presented in Table 2.

Example 3

Figure 10:
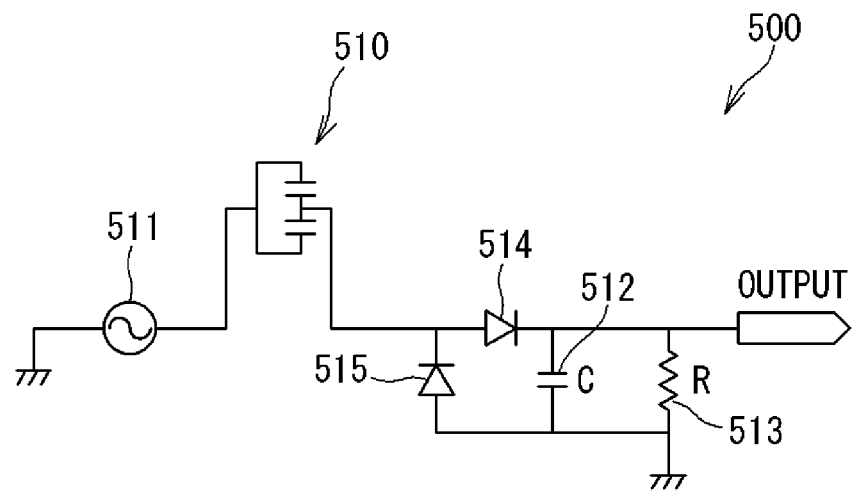
FIG. 10 is a schematic diagram illustrating a half-wave voltage doubler rectifier circuit used for the measurement of capacitance in Example 3 and Comparative Example 3.

A half-wave voltage doubler rectifier circuit 500 as illustrated in FIG. 10 was used as a measuring instrument, this was connected to the sensor sheet A (in FIG. 10, 510), and the output voltage was measured. For the half-wave voltage doubler rectifier circuit 500, the oscillation frequency of an alternating current impression apparatus 511 was set to 5 kHz, the capacitance of a condenser 512 was set to 0.1 µF, the central electrode layer was connected to the alternating current impression apparatus 511, and the top electrode layer and the bottom electrode layer were connected, in a state of being short-circuited, to the OUTPUT side, was designated as reverse connection. For the respective wiring conditions, measurement was made in a noise state of the cases (i) to (iii). The results are presented in Table 2.

Comparative Example 3

A half-wave voltage doubler rectifier circuit 500 similar to that used in Example 3 was used as a measuring instrument, this was connected to the sensor sheet B, and the output voltage was measured.

At this time, the wiring condition in which the top electrode layer was connected to the OUTPUT side, and the bottom electrode layer was connected to the alternating current impression apparatus 511, was designated as proper connection. In contrast, the wiring condition in which the top electrode layer was connected to the alternating current impression apparatus 511, and the bottom electrode layer was connected to the OUTPUT side, was designated as reverse connection. For the various wiring conditions, measurement was made in a noise state of the case (i) or (ii). The results are presented in Table 2.

TABLE 2

| | | | Example 1/Comparative Example 1 Measuring instrument: Inverting amplifier circuit | | Example 2/Comparative Example 2 Measuring instrument: Schmitt trigger oscillator circuit | | | Example 3/Comparative Example 3 Measuring instrument: Half-wave voltage doubler rectifier circuit | | | |
|---|---|---|---|---|---|---|---|---|---|---|---|
| | | | | | | | | Resistance R: 33 kΩ | | Resistance R: 470 kΩ | |
| | | | Noise source: 60 Hz, −2.5 to 2.5 V | | | | | Noise source: 10 kHz, −1.0 to 1.0 V | | | |
| Sensor sheet | Connection mode | Noise surface | Capacitance (PF) | Error (%) | Output (kHz) | Capacitance (PF) | Error (%) | Output (V) | Error (%) | Output (V) | Error (%) |
| B | Proper connection | None | 223 | — | 5.07 | 282 | — | 0.681 | — | 1.302 | — |
| | | Single surface | 221 | 0.9 | 5.06 | 283 | 0.2 | 0.686 | 0.7 | 1.287 | 1.2 |
| | Reverse connection | Single surface | 414 | 46.2 | 3.45 | 414 | 31.3 | 1.373 | 50.4 | 1.780 | 26.9 |
| A | Proper connection | None | 448 | — | 2.66 | 537 | — | 1.170 | — | 1.761 | — |
| | | Single surface | 456 | 1.8 | 2.66 | 537 | 0.0 | 1.161 | 0.8 | 1.747 | 0.8 |
| | | Both surfaces | 456 | 1.8 | 2.66 | 537 | 0.0 | 1.160 | 0.9 | 1.747 | 0.8 |
| | Reverse connection | None | 443 | — | 2.56 | 558 | — | 1.167 | — | 1.713 | — |
| | | Single surface | 497 | 10.8 | 1.97 | 726 | 23.0 | 2.385 | 51.1 | 2.310 | 25.8 |
| | | Both surfaces | 442 | 0.4 | 1.97 | 726 | 23.0 | 2.388 | 51.1 | 2.310 | 25.8 | and the resistance value of a resistor 513 was set to 33 kΩ or 470 kΩ. Furthermore, Schottky diodes were used as diodes 514 and 515.

At this time, the wiring condition in which the central electrode layer was connected to the OUTPUT side, and the top electrode layer and the bottom electrode layer were connected, in a state of being short-circuited, to the alternating current impression apparatus 511, was designated as proper connection. In contrast, the wiring condition in which From the results shown in Table 2, it became clear that in a capacitive sensor including the sensor sheet A, with proper connection, the measured values were not affected, irrespective of whether the noise source was on a single side, or on both sides.

On the other hand, it became clear that in a capacitive sensor including the sensor sheet B, the measured values were not affected by noise from a single side in proper connection; however, the measured values were largely affected by noise from a single side on the opposite side. Of course, in the sensor sheet B, the measured values were similarly largely affected even in a case where noise sources were present on both sides.

Example 4/Comparative Example 4

In the respective cases of sensor sheet A (Example 4) and sensor sheet B (Comparative Example 4), copper foil was installed on both surfaces of the sensor sheet such that the entirety of the detection portion of the sensor sheet would be covered as viewed in a planar view, the copper foil on both surfaces were brought to a state of being electrically connected, and capacitance was measured in this state using a LCR meter in the same manner as for the confirmation of the initial performance.

At this time, the measurement frequency of the LCR meter was set to 5 kHz, the connection between the sensor sheet A and the LCR meter was achieved according to the connection state B, while the connection between the sensor sheet B and the LCR meter was achieved according to the connection state C.

Meanwhile, no noise was applied to the copper foil.

As a result, the capacitance of the sensor sheet A was 502.7 pF, and the capacitance changed by 1.0 pF, compared to the capacitance of the initial performance measured without installing copper foil (501.7 pF (see Table 1)).

On the other hand, the capacitance of the sensor sheet B was 370.9 pF, and the capacitance changed by 118.2 pF, compared to the capacitance of the initial performance measured without installing copper foil (252.7 pF (see Table 1)).

As such, it became clear that in a case where the sensor sheet B was sandwiched between conductors that were electrically connected, capacitance of the sensor sheet B changed significantly; however, capacitance of the sensor sheet A almost did not change even in a case where the sensor sheet A was sandwiched between conductors that were electrically connected.

Regarding the reason for this, it may be considered that in the sensor sheet B, the combined capacitance obtainable from the capacitance between the top electrode layer and the copper foil that was brought close to this top electrode layer, and the capacitance between the bottom electrode layer and the copper foil that was brought close to this bottom electrode layer, the two capacitances being connected in series, was connected in parallel with the capacitance of the detection portion intrinsic to the sensor sheet, so that the capacitance was measured as an added value. With the configuration of the sensor sheet B, the measured value of capacitance was calculated to be increased to 1.50 times through the addition, while the measured value was 1.47 times. Therefore, it became clear that the speculation was right.

On the other hand, in the sensor sheet A, the top electrode layer and the bottom electrode layer were connected, in a state of being short-circuited, to the measuring instrument (LCR meter). Since the two electrode layers were at the same potential level, there was no route through which capacitance between the top electrode layer or the bottom electrode layer and the copper foil would intervene unlike the case of the sensor sheet B, and the measured value of capacitance measured at the detection portion was not added.

From the above results, it became clear that a capacitive sensor including the sensor sheet A would be not easily affected by the environment of measurement.

Example 5

The entirety of electrically conductive sites of sensor sheet A (various conducting wire parts, various connecting portions, terminals of lead wires, and the like), which were exposed to the outside, was covered with an insulating adhesive for electronic components (Cemedine Co., Ltd., SX720B) so as to make the electrically conductive members not to be exposed to the outside. Subsequently, the sensor sheet A was connected to a LCR meter. The connection between the sensor sheet A and the LCR meter was achieved in the same manner as in the connection state B described with regard to the confirmation of initial performance as described above (frequency was 5 kHz).

First, the total capacitance Ct in air of the sensor sheet A was measured. As a result, the total capacitance Ct was 497.5 pF.

Next, the entirety of the sensor sheet A was immersed in ion-exchanged water, and after a lapse of 1 minute, the total capacitance Ct was measured. As a result, the total capacitance Ct was 525.7 pF, and it was implied that the total capacitance had increased by 28.2 pF.

Comparative Example 5

The entirety of electrically conductive sites of sensor sheet B (various conducting wire parts, various connecting portions, terminals of lead wires, and the like), which were exposed to the outside, was covered with an insulating adhesive so as to make the electrically conductive members not to be exposed to the outside. Subsequently, the sensor sheet B was connected to a LCR meter. The connection between the sensor sheet B and the LCR meter was achieved in the same manner as in the connection state C described with regard to the confirmation of initial performance as described above (frequency was 5 kHz).

First, the capacitance in air of the sensor sheet B was measured. As a result, the capacitance was 248.2 pF.

Next, the entirety of the sensor sheet B was immersed in ion-exchanged water, and after a lapse of 1 minute, the capacitance was measured. As a result, the capacitance was 405.6 pF, and it was implied that the total capacitance had increased by 157.4 pF.

From the results of Example 5 and Comparative Example 5, it became clear that in a capacitive sensor including the sensor sheet A, the change in capacitance at the detection portion was small, even if the capacitive sensor was used in a state in which the surface was wet, compared to a capacitive sensor including the sensor sheet B.

From these results, it is contemplated that the above-described capacitive sensor can be suitably used even in a use environment such as that the capacitive sensor is used in an environment in which a sensor sheet is wetted with sweat or the like, for example, the capacitive sensor is used by being attached to the body at the time of exercise.

REFERENCE SIGNS LIST

1 Capacitive sensor
2, 2' Sensor sheet
3 Measuring instrument
3a, 400 Schmitt trigger oscillator circuit
3b F/V conversion circuit
4 Display device
4a Monitor
4b Arithmetic circuit
4c Memory unit 11A, 120 Top dielectric layer (first dielectric layer)
11B, 130 Bottom dielectric layer (second dielectric layer)
12A, 101A to 116A Central electrode layer
12B, 101B to 116B Top electrode layer (first outer electrode layer)
12C, 101C to 116C Bottom electrode layer (second outer electrode layer)
13A Central conducting wire
13B Top conducting wire
13C Bottom conducting wire
14A Central connecting portion
14B Top connecting portion
14C Bottom connecting portion
15A, 140 Top protective layer (first protective layer)
15B, 150 Bottom protective layer (second protective layer)
101A1 to 116A1, 101B1 to 116B1 Connecting portion
300 Inverting amplifier circuit
500 Half-wave voltage doubler rectifier circuit

The invention claimed is:

1. A capacitive sensor comprising a sensor sheet and a measuring instrument,
the sensor sheet including:
a central electrode layer;
a first dielectric layer laminated on the upper surface of the central electrode layer;
a second dielectric layer laminated on the lower surface of the central electrode layer;
a first outer electrode layer formed on the surface of the first dielectric layer on the opposite side of the central electrode layer side; and
a second outer electrode layer formed on the surface of the second dielectric layer on the opposite side of the central electrode layer side,
in which the first dielectric layer and the second dielectric layer are formed from elastomers,
the part where the central electrode layer and the first outer electrode layer face each other is designated as a first detection portion, while the part where the central electrode layer and the second outer electrode layer face each other is designated as a second detection portion,
the sensor sheet is reversibly deformable, and the capacitances of the first detection portion and the second detection portion change with deformation, and
the measuring instrument being connected to the central electrode layer, the first outer electrode layer and the second outer electrode layer and measuring the capacitances of the first detection portion and the second detection portion,
wherein the first dielectric layer and the second dielectric layer are deformed in a surface direction; and
the state of deformation of the sensor sheet is measured on the basis of the total capacitance by adding the capacitance of the first detection portion and the capacitance of the second detection portion.

2. The capacitive sensor according to claim 1, wherein the central electrode layer, the first outer electrode layer and the second outer electrode layer are all formed from electroconductive compositions containing carbon nanotubes.

3. The capacitive sensor according to claim 1, wherein the sensor sheet further includes at least one of a first protective layer laminated on the first outer electrode layer on the opposite side of the first dielectric layer side, and a second protective layer laminated on the second outer electrode layer on the opposite side of the second dielectric layer side.

4. The capacitive sensor according to claim 1, wherein the measuring instrument includes a circuit capable of measuring capacitance using alternating current impedance.

5. The capacitive sensor according to claim 4, wherein the measuring instrument includes a CV conversion circuit, the central electrode layer is electrically connected to the CV conversion circuit side, and the first outer electrode layer and the second outer electrode layer are electrically connected to the alternating current signal generation side of the measuring instrument.

6. The capacitive sensor according to claim 4, wherein the measuring instrument includes a CF conversion circuit, the central electrode layer is electrically connected to the CF conversion circuit side, and the first outer electrode layer and the second outer electrode layer are grounded.

* * * * *